United States Patent
Lyon et al.

(10) Patent No.: US 12,029,852 B2
(45) Date of Patent: Jul. 9, 2024

(54) SYSTEMS AND METHODS FOR DETECTING RAINOUT IN A RESPIRATORY THERAPY SYSTEM

(71) Applicant: ResMed Sensor Technologies Limited, Dublin (IE)

(72) Inventors: Graeme Alexander Lyon, Dublin (IE); Niall Andrew Fox, Dublin (IE); Roxana Tiron, Dublin (IE); Stephen McMahon, Dublin (IE)

(73) Assignee: ResMed Sensor Technologies Limited, Dublin (IE)

( * ) Notice: Subject to any disclaimer, the term of this patent is extended or adjusted under 35 U.S.C. 154(b) by 0 days.

(21) Appl. No.: 18/257,096

(22) PCT Filed: Dec. 22, 2021

(86) PCT No.: PCT/IB2021/062219
§ 371 (c)(1),
(2) Date: Jun. 12, 2023

(87) PCT Pub. No.: WO2022/137183
PCT Pub. Date: Jun. 30, 2022

(65) Prior Publication Data
US 2024/0033459 A1 Feb. 1, 2024

Related U.S. Application Data

(60) Provisional application No. 63/130,316, filed on Dec. 23, 2020.

(51) Int. Cl.
*A61M 16/00* (2006.01)

(52) U.S. Cl.
CPC ... *A61M 16/026* (2017.08); *A61M 2205/3375* (2013.01)

(58) Field of Classification Search
CPC ........ A61M 2205/3375; A61M 16/024; A61M 16/16; A61M 16/026; A61M 16/0477
See application file for complete search history.

(56) References Cited

U.S. PATENT DOCUMENTS

| 5,245,995 A | 9/1993 | Sullivan et al. |
| 5,823,965 A | 10/1998 | Rasmussen |

(Continued)

FOREIGN PATENT DOCUMENTS

| WO | 2008/138040 A1 | 11/2008 |
| WO | 2014/047310 A1 | 3/2014 |

(Continued)

OTHER PUBLICATIONS

International Search Report in International Patent Application No. PCT/IB2021/062219 dated Apr. 4, 2022 (5 pp.).

(Continued)

*Primary Examiner* — Margaret M Luarca
(74) *Attorney, Agent, or Firm* — Nixon Peabody LLP

(57) ABSTRACT

A method of detecting rainout in a respiratory therapy system that includes a conduit fluidly coupled to a user interface comprises generating, via at least one microphone, acoustic data representative of noise associated with the respiratory therapy system. The method further comprises analyzing the acoustic data to detect a presence of liquid in the respiratory therapy system. The method further comprises causing an action to be performed, based on the detected presence of the liquid.

36 Claims, 7 Drawing Sheets

(56) References Cited

U.S. PATENT DOCUMENTS

| | | |
|---|---|---|
| 6,502,572 B1 | 1/2003 | Berthon-Jones et al. |
| 9,358,353 B2 | 6/2016 | Armitstead et al. |
| 10,492,720 B2 | 12/2019 | Phillips et al. |
| 10,660,563 B2 | 5/2020 | McDarby et al. |
| 2013/0255691 A1* | 10/2013 | Mansfield ............ A61M 16/04 128/207.14 |
| 2017/0311879 A1 | 11/2017 | Armitstead et al. |
| 2020/0337634 A1 | 10/2020 | McDarby et al. |
| 2020/0376218 A1 | 12/2020 | Mansfield et al. |
| 2020/0383580 A1 | 12/2020 | Shouldice et al. |
| 2021/0150873 A1 | 5/2021 | Shouldice et al. |

FOREIGN PATENT DOCUMENTS

| | | |
|---|---|---|
| WO | 2016/061629 A1 | 4/2016 |
| WO | 2017/132726 A1 | 8/2017 |
| WO | 2018/050913 A1 | 3/2018 |
| WO | 2019/006496 A1 | 1/2019 |
| WO | 2019/122413 A1 | 6/2019 |
| WO | 2019/122414 A1 | 6/2019 |
| WO | 2020/104465 A2 | 5/2020 |

OTHER PUBLICATIONS

Written Opinion in International Patent Application No. PCT/IB2021/062219 dated Apr. 4, 2022 (8 pp.).

* cited by examiner

SYSTEMS AND METHODS FOR DETECTING RAINOUT IN A RESPIRATORY THERAPY SYSTEM

CROSS-REFERENCE TO RELATED APPLICATIONS

This application is a U.S. National Stage of International Application No. PCT/IB2021/062219, filed on Dec. 22, 2021, which claims the benefit of, and priority to, U.S. Provisional Patent Application No. 63/130,316 filed on Dec. 23, 2020, each of which is hereby incorporated by reference herein in its entirety.

TECHNICAL FIELD

The present disclosure relates generally to systems and methods for detecting the presence of liquid in a conduit of a respiratory therapy system, and more particularly, to systems and methods for using acoustic data to detect the presence of liquid in a conduit of a respiratory therapy system, and removing the liquid from the conduit of the respiratory therapy system.

BACKGROUND

Many individuals suffer from sleep-related and/or respiratory disorders such as, for example, Sleep-Disordered Breathing (SDB), which can include Obstructive Sleep Apnea (OSA), Central Sleep Apnea (CSA), other types of apneas such as mixed apneas and hypopneas, and Respiratory Effort Related Arousal (RERA). These individuals may also suffer from other health conditions (which may be referred to as comorbidities), such as insomnia (characterized by, for example, difficult in initiating sleep, frequent or prolonged awakenings after initially falling asleep, and/or an early awakening with an inability to return to sleep), Periodic Limb Movement Disorder (PLMD), Restless Leg Syndrome (RLS), Cheyne-Stokes Respiration (CSR), respiratory insufficiency, Obesity Hyperventilation Syndrome (OHS), Chronic Obstructive Pulmonary Disease (COPD), Neuromuscular Disease (NMD), rapid eye movement (REM) behavior disorder (also referred to as RBD), dream enactment behavior (DEB), hypertension, diabetes, stroke, and chest wall disorders. These individuals are often treated using a respiratory therapy system (e.g., a continuous positive airway pressure (CPAP) system), which delivers pressurized air to aid in preventing the individual's airway from narrowing or collapsing during sleep. The respiratory therapy system can generate physiological data associated with a sleep session, which in turn can be used to determine sleep-related parameters and/or generate reports indicative of sleep quality. The respiratory therapy system can include a conduit that delivers pressurized air from a respiratory therapy device having a flow generator (e.g., a motor), to a user interface coupled to the individual's face.

In certain situations, liquid can accumulate in the conduit or in the user interface, a phenomenon referred to as rainout. For example, a reservoir of water can be heated so as to humidify the pressurized air before being directed to the individual's airway. If the humidified air cools within the conduit, the water can undergo condensation, such that liquid water can begin to fill the conduit and/or the user interface. Thus, accumulation of water in the conduit and/or the user interface often results in a gurgling noise, which can wake the individual during their use of the respiratory therapy system, and/or disturb or wake a bed partner of the user. In some cases, the liquid can dampen or saturate the user interface as well, for example if the user interface includes foam or another soft and/or absorbent material. Saturation of the user interface, or at least a portion of the user interface becoming damp, can also wake the individual and result in the individual experiencing anxiety and claustrophobia. Thus, it would be beneficial to be able to detect the presence of liquid in the conduit and/or the user interface, and further to remove this liquid and/or prevent the accumulation of liquid in the conduit and/or the user interface in the future. The present disclosure is directed to solving this and other problems.

SUMMARY

According to some implementations of the present disclosure, a method for detecting rainout in a respiratory therapy system comprises generating, via at least one microphone, acoustic data representative of noise associated with a respiratory therapy system; analyzing the acoustic data to detect a presence of liquid in the respiratory therapy system; and based on the detected presence of the liquid, causing an action to be performed.

According to some implementations of the present disclosure, the noise associated with the respiratory therapy system is caused by the presence of the liquid in the conduit, in the user interface, or both. The noise caused by the presence of the liquid in the respiratory therapy system results in a corresponding acoustic signature in the acoustic data, and wherein analyzing the acoustic data includes identifying the acoustic signature of the noise caused by the presence of the liquid in the respiratory therapy system.

According to some implementations of the present disclosure, the action includes modifying a temperature of the conduit, modifying a temperature of a humidification tank of the respiratory therapy system, modifying a temperature of an ambient environment around the conduit, sending a notification to a user of the respiratory therapy system or to a third party, sending a recommendation to the user or to the third party to reduce or remove the liquid in the respiratory therapy system, reversing a direction of a motor of the respiratory therapy system, increasing a rate of flow of pressurized air through the conduit, or any combination thereof.

According to some implementations of the present disclosure, the acoustic data is generated prior to a beginning of sleep session, during the sleep session, or after the completion of the sleep session.

According to some implementations of the present disclosure, a method for detecting rainout in a respiratory therapy system comprises generating, via at least one microphone, first acoustic data representative of noise associated with the respiratory therapy system; analyzing the first acoustic data to detect a presence of liquid in the respiratory therapy system; transmitting, to a user of the respiratory therapy system, (i) a notification of the presence of the liquid in the respiratory therapy system and (ii) a recommendation for action to reduce or remove the liquid in the respiratory therapy system; generating, via the at least one microphone, second acoustic data representative of noise associated with the respiratory therapy system; analyzing the second acoustic data to determine an amount of the liquid remaining in the respiratory therapy system following the action; and in response to determining that the amount of the liquid remaining in the respiratory therapy system is less than a threshold amount, transmitting to the user a notification that the amount of liquid remaining in the respiratory therapy system is less than the threshold amount.

According to some implementations of the present disclosure, a system comprises a respiratory therapy system, at least one microphone, a memory device, and a control system. The respiratory therapy system includes a respiratory therapy device, and a user interface coupled to the respiratory therapy device via a conduit. The respiratory therapy device is configured to supply pressurized air. The user interface is configured to engage a user and aid in directing the supplied pressurized air to an airway of the user. The memory device stores machine-readable instructions. The control system is coupled to the memory device, and is configured to execute the machine-readable instructions to generate, via the at least one microphone, acoustic data representative of noise associated with the respiratory therapy system. The control system is further configured to execute the machine-readable instructions to analyze the acoustic data to detect a presence of liquid in the respiratory therapy system. The control system is further configured to execute the machine-readable instructions to, based on the detected presence of the liquid, cause an action to be performed.

According to some implementations of the present disclosure, a system comprises a respiratory therapy system, at least one microphone, a memory device, and a control system. The respiratory therapy system includes a respiratory therapy device, and a user interface coupled to the respiratory therapy device via a conduit. The respiratory therapy device is configured to supply pressurized air. The user interface is configured to engage a user and aid in directing the supplied pressurized air to an airway of the user. The memory device stores machine-readable instructions. The control system is coupled to the memory device, and is configured to execute the machine-readable instructions to generate, via the at least one microphone, first acoustic data representative of noise associated with the respiratory therapy system. The control system is further configured to execute the machine-readable instructions to analyze the first acoustic data to detect a presence of liquid in the respiratory therapy system. The control system is further configured to execute the machine-readable instructions to transmit, to the user of the respiratory therapy system, (i) a notification of the presence of the liquid in the respiratory therapy system and (ii) a recommendation for action to reduce or remove the liquid in the respiratory therapy system. The control system is further configured to execute the machine-readable instructions to generate, via the at least one microphone, second acoustic data representative of noise associated with the respiratory therapy system. The control system is further configured to execute the machine-readable instructions to analyze the second acoustic data to determine an amount of the liquid remaining in the respiratory therapy system following the action. The control system is further configured to execute the machine-readable instructions to, in response to determining that the amount of the liquid remaining in the respiratory therapy system is less than a threshold amount, transmit to the user a notification that the amount of liquid remaining in the respiratory therapy system is less than the threshold amount.

The above summary is not intended to represent each embodiment or every aspect of the present invention. Additional features and benefits of the present invention are apparent from the detailed description and figures set forth below.

Figure 1:
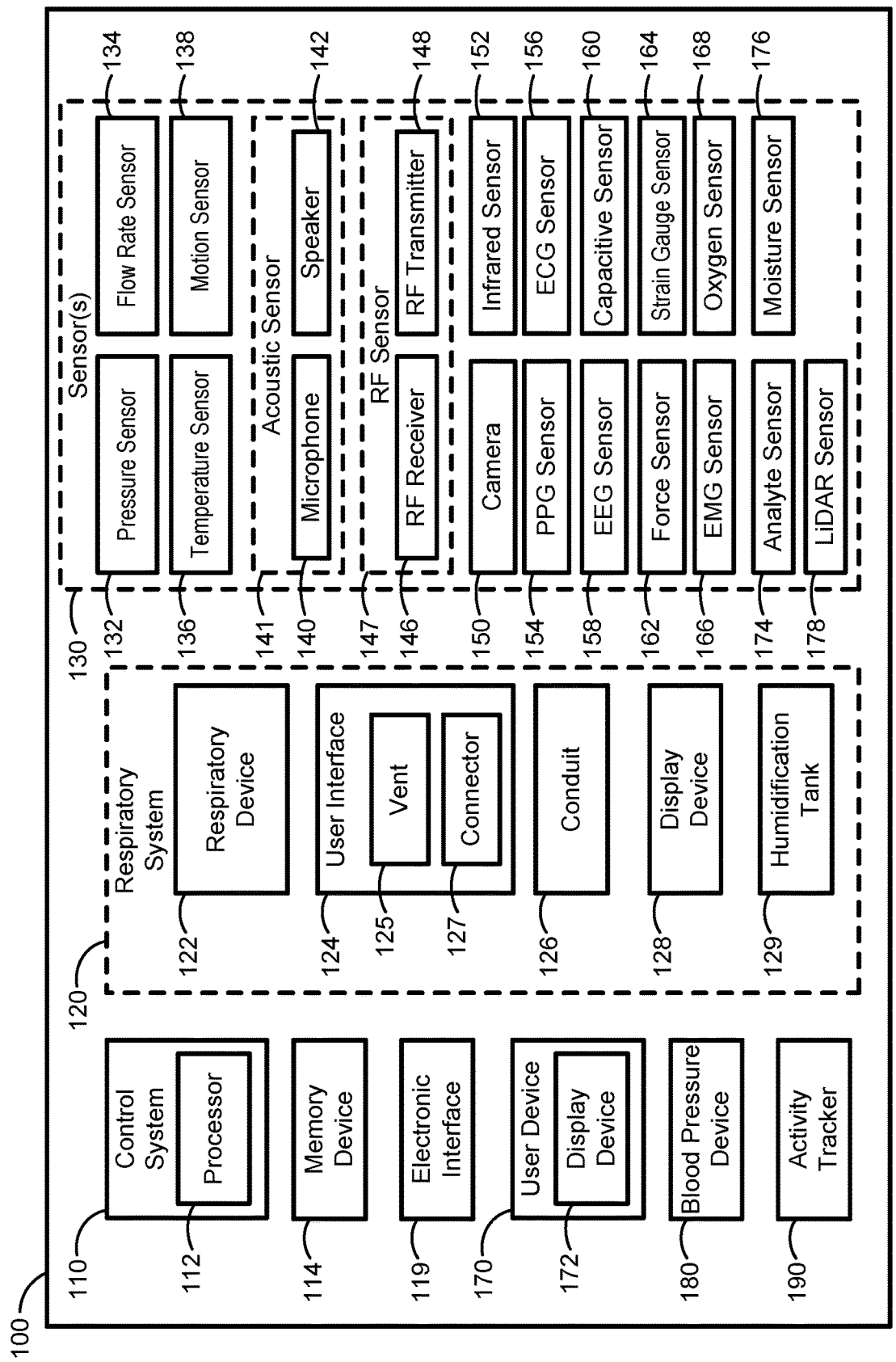
FIG. 1 is a functional block diagram of a system for detecting rainout in a respiratory therapy system, according to some implementations of the present disclosure.

While the present disclosure is susceptible to various modifications and alternative forms, specific implementations and embodiments thereof have been shown by way of example in the drawings and will herein be described in detail. It should be understood, however, that it is not intended to limit the present disclosure to the particular forms disclosed, but on the contrary, the present disclosure is to cover all modifications, equivalents, and alternatives falling within the spirit and scope of the present disclosure as defined by the appended claims.

DETAILED DESCRIPTION

The present disclosure is described with reference to the attached figures, where like reference numerals are used throughout the figures to designate similar or equivalent elements. The figures are not drawn to scale, and are provided merely to illustrate the instant disclosure. Several aspects of the disclosure are described below with reference to example applications for illustration.

Many individuals suffer from sleep-related and/or respiratory disorders. Examples of sleep-related and/or respiratory disorders include Periodic Limb Movement Disorder (PLMD), Restless Leg Syndrome (RLS), Sleep-Disordered Breathing (SDB), Obstructive Sleep Apnea (OSA), Central Sleep Apnea (CSA), other types of apneas, Cheyne-Stokes Respiration (CSR), respiratory insufficiency, Obesity Hyperventilation Syndrome (OHS), Chronic Obstructive Pulmonary Disease (COPD), Neuromuscular Disease (NMD), and chest wall disorders.

Many individuals suffer from sleep-related and/or respiratory disorders, such as Periodic Limb Movement Disorder (PLMD), Restless Leg Syndrome (RLS), Sleep-Disordered Breathing (SDB) such as Obstructive Sleep Apnea (OSA), Central Sleep Apnea (CSA) and other types of apneas, Respiratory Effort Related Arousal (RERA), Cheyne-Stokes Respiration (CSR), respiratory insufficiency, Obesity Hyperventilation Syndrome (OHS), Chronic Obstructive Pulmonary Disease (COPD), Neuromuscular Disease (NMD), and chest wall disorders. Obstructive Sleep Apnea (OSA), a form of Sleep Disordered Breathing (SDB), is characterized by events including occlusion or obstruction of the upper air passage during sleep resulting from a combination of an abnormally small upper airway and the normal loss of muscle tone in the region of the tongue, soft palate and posterior oropharyngeal wall. Central Sleep Apnea (CSA) is another form of sleep disordered breathing. CSA results when the brain temporarily stops sending signals to the muscles that control breathing. Other types of apneas include hypopnea, hyperpnea, and hypercapnia. Hypopnea is generally characterized by slow or shallow breathing caused by a narrowed airway, as opposed to a blocked airway. Hyperpnea is generally characterized by an increase depth and/or rate of breathing. Hypercapnia is generally characterized by elevated or excessive carbon dioxide in the bloodstream, typically caused by inadequate respiration. A Respiratory Effort Related Arousal (RERA) event is typically characterized by an increased respiratory effort for ten seconds or longer leading to arousal from sleep and which does not fulfill the criteria for an apnea or hypopnea event. RERAs are defined as a sequence of breaths characterized by increasing respiratory effort leading to an arousal from sleep, but which does not meet criteria for an apnea or hypopnea. These events must fulfil both of the following criteria: (1) a pattern of progressively more negative esophageal pressure, terminated by a sudden change in pressure to a less negative level and an arousal, and (2) the event lasts ten seconds or longer. In some implementations, a Nasal Cannula/Pressure Transducer System is adequate and reliable in the detection of RERAs. A RERA detector may be based on a real flow signal derived from a respiratory therapy device. For example, a flow limitation measure may be determined based on a flow signal. A measure of arousal may then be derived as a function of the flow limitation measure and a measure of sudden increase in ventilation. One such method is described in WO 2008/138040 and U.S. Pat. No. 9,358,353, assigned to ResMed Ltd., the disclosure of each of which is hereby incorporated by reference herein in their entireties.

Cheyne-Stokes Respiration (CSR) is a further form of SDB. CSR is a disorder of a patient's respiratory controller in which there are rhythmic alternating periods of waxing and waning ventilation known as CSR cycles. CSR is characterized by repetitive de-oxygenation and re-oxygenation of the arterial blood. OHS is defined as the combination of severe obesity and awake chronic hypercapnia, in the absence of other known causes for hypoventilation. Symptoms include dyspnea, morning headache and excessive daytime sleepiness. COPD encompasses any of a group of lower airway diseases that have certain characteristics in common, such as increased resistance to air movement, extended expiratory phase of respiration, and loss of the normal elasticity of the lung. NMD encompasses many diseases and ailments that impair the functioning of the muscles either directly via intrinsic muscle pathology, or indirectly via nerve pathology. Chest wall disorders are a group of thoracic deformities that result in inefficient coupling between the respiratory muscles and the thoracic cage.

Many of these disorders are characterized by particular events (e.g., snoring, an apnea, a hypopnea, a restless leg, a sleeping disorder, choking, an increased heart rate, labored breathing, an asthma attack, an epileptic episode, a seizure, or any combination thereof) that can occur when the individual is sleeping. A wide variety of types of data can be used to monitor the health of individuals having any of the above types of sleep-related and/or respiratory disorders (or other disorders).

The Apnea-Hypopnea Index (AHI) is an index used to indicate the severity of sleep apnea during a sleep session. The AHI is calculated by dividing the number of apnea and/or hypopnea events experienced by the user during the sleep session by the total number of hours of sleep in the sleep session. The event can be, for example, a pause in breathing that lasts for at least 10 seconds. An AHI that is less than 5 is considered normal. An AHI that is greater than or equal to 5, but less than 15 is considered indicative of mild sleep apnea. An AHI that is greater than or equal to 15, but less than 30 is considered indicative of moderate sleep apnea. An AHI that is greater than or equal to 30 is considered indicative of severe sleep apnea. In children, an AHI that is greater than 1 is considered abnormal. Sleep apnea can be considered "controlled" when the AHI is normal, or when the AHI is normal or mild. The AHI can also be used in combination with oxygen desaturation levels to indicate the severity of Obstructive Sleep Apnea.

Referring to FIG. 1, a system 100, according to some implementations of the present disclosure, is illustrated. The system 100 includes a control system 110, a memory device 114, an electronic interface 119, one or more sensors 130, and optionally one or more user devices 170. In some implementations, the system 100 further includes a respiratory therapy system 120 (that includes a respiratory therapy device 122), a blood pressure device 180, an activity tracker 190, or any combination thereof. The system 100 can be used to detect rainout (e.g., the presence of liquid) in the respiratory therapy system 120 during use.

The control system 110 includes one or more processors 112 (hereinafter, processor 112). The control system 110 is generally used to control (e.g., actuate) the various components of the system 100 and/or analyze data obtained and/or generated by the components of the system 100. The processor 112 can be a general or special purpose processor or microprocessor. While one processor 112 is shown in FIG. 1, the control system 110 can include any suitable number of processors (e.g., one processor, two processors, five processors, ten processors, etc.) that can be in a single housing, or located remotely from each other. The control system 110 (or any other control system) or a portion of the control system 110 such as the processor 112 (or any other processor(s) or portion(s) of any other control system), can be used to carry out one or more steps of any of the methods described and/or claimed herein. The control system 110 can be coupled to and/or positioned within, for example, a housing of the user device 170, and/or within a housing of one or more of the sensors 130. The control system 110 can be centralized (within one such housing) or decentralized (within two or more of such housings, which are physically distinct). In such implementations including two or more housings containing the control system 110, such housings can be located proximately and/or remotely from each other.

The memory device 114 stores machine-readable instructions that are executable by the processor 112 of the control system 110. The memory device 114 can be any suitable computer readable storage device or media, such as, for example, a random or serial access memory device, a hard drive, a solid state drive, a flash memory device, etc. While one memory device 114 is shown in FIG. 1, the system 100 can include any suitable number of memory devices 114 (e.g., one memory device, two memory devices, five memory devices, ten memory devices, etc.). The memory device 114 can be coupled to and/or positioned within a housing of the respiratory therapy device 122 of the respiratory therapy system 120, within a housing of the user device 170, within a housing of one or more of the sensors 130, or any combination thereof. Like the control system 110, the memory device 114 can be centralized (within one such housing) or decentralized (within two or more of such housings, which are physically distinct).

In some implementations, the memory device 114 stores a user profile associated with the user. The user profile can include, for example, demographic information associated with the user, biometric information associated with the user, medical information associated with the user, self-reported user feedback, sleep parameters associated with the user (e.g., sleep-related parameters recorded from one or more earlier sleep sessions), or any combination thereof. The demographic information can include, for example, information indicative of an age of the user, a gender of the user, a race of the user, a family medical history (such as a family history of insomnia or sleep apnea), an employment status of the user, an educational status of the user, a socioeconomic status of the user, or any combination thereof. The medical information can include, for example, information indicative of one or more medical conditions associated with the user, medication usage by the user, or both. The medical information data can further include a fall risk assessment associated with the user (e.g., a fall risk score using the Morse fall scale), a multiple sleep latency test (MSLT) result or score and/or a Pittsburgh Sleep Quality Index (PSQI) score or value. The self-reported user feedback can include information indicative of a self-reported subjective sleep score (e.g., poor, average, excellent), a self-reported subjective stress level of the user, a self-reported subjective fatigue level of the user, a self-reported subjective health status of the user, a recent life event experienced by the user, or any combination thereof.

The electronic interface 119 is configured to receive data (e.g., physiological data and/or acoustic data) from the one or more sensors 130 such that the data can be stored in the memory device 114 and/or analyzed by the processor 112 of the control system 110. The electronic interface 119 can communicate with the one or more sensors 130 using a wired connection or a wireless connection (e.g., using an RF communication protocol, a WiFi communication protocol, a Bluetooth communication protocol, an IR communication protocol, over a cellular network, over any other optical communication protocol, etc.). The electronic interface 119 can include an antenna, a receiver (e.g., an RF receiver), a transmitter (e.g., an RF transmitter), a transceiver, or any combination thereof. The electronic interface 119 can also include one or more processors and/or one or more memory devices that are the same as, or similar to, the processor 112 and the memory device 114 described herein. In some implementations, the electronic interface 119 is coupled to or integrated in the user device 170. In other implementations, the electronic interface 119 is coupled to or integrated (e.g., in a housing) with the control system 110 and/or the memory device 114.

As noted above, in some implementations, the system 100 optionally includes a respiratory therapy system 120 (also referred to as a respiratory pressure therapy system). The respiratory therapy system 120 can include a respiratory therapy device 122 (also referred to as a respiratory pressure device), a user interface 124 (also referred to as a mask or a patient interface), a conduit 126 (also referred to as a tube or an air circuit), a display device 128, a humidification tank 129, or any combination thereof. In some implementations, the control system 110, the memory device 114, the display device 128, one or more of the sensors 130, and the humidification tank 129 are part of the respiratory therapy device 122. Respiratory pressure therapy refers to the application of a supply of air to an entrance to a user's airways at a controlled target pressure that is nominally positive with respect to atmosphere throughout the user's breathing cycle (e.g., in contrast to negative pressure therapies such as the tank ventilator or cuirass). The respiratory therapy system 120 is generally used to treat individuals suffering from one or more sleep-related respiratory disorders (e.g., obstructive sleep apnea, central sleep apnea, or mixed sleep apnea), other respiratory disorders such as COPD, or other disorders leading to respiratory insufficiency, that may manifest either during sleep or wakefulness.

The respiratory therapy device 122 is generally used to generate pressurized air that is delivered to a user (e.g., using one or more motors (such as a blower motor) that drive one or more compressors). In some implementations, the respiratory therapy device 122 generates continuous constant air pressure that is delivered to the user. In other implementations, the respiratory therapy device 122 generates two or more predetermined pressures (e.g., a first predetermined air pressure and a second predetermined air pressure). In still other implementations, the respiratory therapy device 122 is configured to generate a variety of different air pressures within a predetermined range. For example, the respiratory therapy device 122 can deliver at least about 6 cm $H_2O$, at least about 10 cm $H_2O$, at least about 20 cm $H_2O$, between about 6 cm $H_2O$ and about 10 cm $H_2O$, between about 7 cm $H_2O$ and about 12 cm $H_2O$, etc. The respiratory therapy device 122 can also deliver pressurized air at a predetermined flow rate between, for example, about −20 L/min and about 150 L/min, while maintaining a positive pressure (relative to the ambient pressure). In some implementations, the control system 110, the memory device 114, the electronic interface 119, or any combination thereof can be coupled to and/or positioned within a housing of the respiratory therapy device 122.

The user interface 124 engages a portion of the user's face and delivers pressurized air from the respiratory therapy device 122 to the user's airway to aid in preventing the airway from narrowing and/or collapsing during sleep. This may also increase the user's oxygen intake during sleep. Depending upon the therapy to be applied, the user interface 124 may form a seal, for example, with a region or portion of the user's face, to facilitate the delivery of gas at a pressure at sufficient variance with ambient pressure to effect therapy, for example, at a positive pressure of about 10 cm $H_2O$ relative to ambient pressure. For other forms of therapy, such as the delivery of oxygen, the user interface may not include a seal sufficient to facilitate delivery to the airways of a supply of gas at a positive pressure of about 10 cm$H_2O$.

Figure 2:
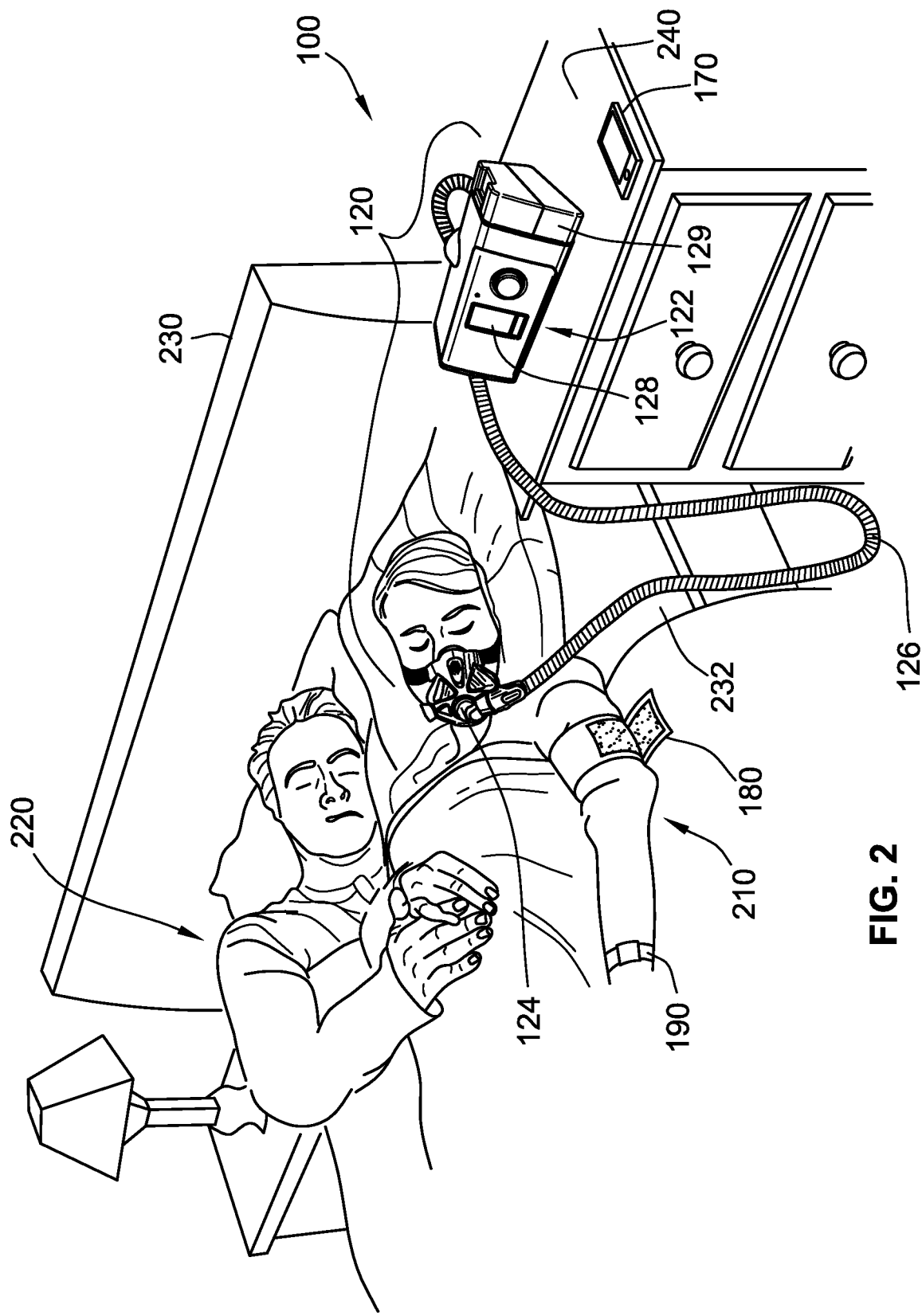
FIG. 2 is a perspective view of the system of FIG. 1, a user of the system, and a bed partner of the user, according to some implementations of the present disclosure.

In some implementations, the user interface 124 is or includes a facial mask that covers the nose and mouth of the user (as shown, for example, in FIG. 2). Alternatively, the user interface 124 is or includes a nasal mask that provides air to the nose of the user or a nasal pillow mask that delivers air directly to the nostrils of the user. The user interface 124 can include a strap assembly that has a plurality of straps (e.g., including hook and loop fasteners) for positioning and/or stabilizing the user interface 124 on a portion of the user interface 124 on a desired location of the user (e.g., the face), and a conformal cushion (e.g., silicone, plastic, foam, etc.) that aids in providing an air-tight seal between the user interface 124 and the user. In some implementations, the user interface 124 may include a connector 127 and one or more vents 125. The one or more vents 125 can be used to permit the escape of carbon dioxide and other gases exhaled by the user. In other implementations, the user interface 124 includes a mouthpiece (e.g., a night guard mouthpiece molded to conform to the user's teeth, a mandibular repositioning device, etc.). In some implementations, the connector 127 is distinct from, but couplable to, the user interface 124 (and/or conduit 126). The connector 127 is configured to connect and fluidly couple the user interface 124 to the conduit 126.

The conduit 126 allows the flow of air between two components of a respiratory therapy system 120, such as the respiratory therapy device 122 and the user interface 124. In some implementations, there can be separate limbs of the conduit for inhalation and exhalation. In other implementations, a single limb conduit is used for both inhalation and exhalation. Generally, the respiratory therapy system 120 forms an air pathway that extends between a motor of the respiratory therapy device 122 and the user and/or the user's airway. Thus, the air pathway generally includes at least a motor of the respiratory therapy device 122, the user interface 124, and the conduit 126.

One or more of the respiratory therapy device 122, the user interface 124, the conduit 126, the display device 128, and the humidification tank 129 can contain one or more sensors (e.g., a pressure sensor, a flow rate sensor, or more generally any of the other sensors 130 described herein). These one or more sensors can be used, for example, to measure the air pressure and/or flow rate of pressurized air supplied by the respiratory therapy device 122.

The display device 128 is generally used to display image(s) including still images, video images, or both and/or information regarding the respiratory therapy device 122. For example, the display device 128 can provide information regarding the status of the respiratory therapy device 122 (e.g., whether the respiratory therapy device 122 is on/off, the pressure of the air being delivered by the respiratory therapy device 122, the temperature of the air being delivered by the respiratory therapy device 122, etc.) and/or other information (e.g., a sleep score or a therapy score (such as a myAir® score, such as described in WO 2016/061629 and US 2017/0311879, each of which is hereby incorporated by reference herein in its entirety), the current date/time, personal information for the user, a questionnaire for the user, etc.). In some implementations, the display device 128 acts as a human-machine interface (HMI) that includes a graphic user interface (GUI) configured to display the image(s) as an input interface. The display device 128 can be an LED display, an OLED display, an LCD display, or the like. The input interface can be, for example, a touchscreen or touch-sensitive substrate, a mouse, a keyboard, or any sensor system configured to sense inputs made by a human user interacting with the respiratory therapy device 122.

The humidification tank 129 is coupled to or integrated in the respiratory therapy device 122 and includes a reservoir of water that can be used to humidify the pressurized air delivered from the respiratory therapy device 122. The respiratory therapy device 122 can include a heater to heat the water in the humidification tank 129 in order to humidify the pressurized air provided to the user. Additionally, in some implementations, the conduit 126 can also include a heating element (e.g., coupled to and/or imbedded in the conduit 126) that heats the pressurized air delivered to the user. The humidification tank 129 can be fluidly coupled to a water vapor inlet of the air pathway and deliver water vapor into the air pathway via the water vapor inlet, or can be formed in-line with the air pathway as part of the air pathway itself. In other implementations, the respiratory therapy device 122 or the conduit 126 can include a waterless humidifier. The waterless humidifier can incorporate sensors that interface with other sensor positioned elsewhere in system 100.

The respiratory therapy system 120 can be used, for example, as a ventilator or a positive airway pressure (PAP) system, such as a continuous positive airway pressure (CPAP) system, an automatic positive airway pressure system (APAP), a bi-level or variable positive airway pressure system (BPAP or VPAP), or any combination thereof. The CPAP system delivers a predetermined air pressure (e.g., determined by a sleep physician) to the user. The APAP system automatically varies the air pressure delivered to the user based at least in part on, for example, respiration data associated with the user. The BPAP or VPAP system is configured to deliver a first predetermined pressure (e.g., an inspiratory positive airway pressure or IPAP) and a second predetermined pressure (e.g., an expiratory positive airway pressure or EPAP) that is lower than the first predetermined pressure.

Referring to FIG. 2, a portion of the system 100 (FIG. 1), according to some implementations, is illustrated. A user 210 of the respiratory therapy system 120 and a bed partner 220 are located in a bed 230 and are laying on a mattress 232. The user interface 124 (e.g., a full facial mask) can be worn by the user 210 during a sleep session. The user interface 124 is fluidly coupled and/or connected to the respiratory therapy device 122 via the conduit 126. In turn, the respiratory therapy device 122 delivers pressurized air to the user 210 via the conduit 126 and the user interface 124 to increase the air pressure in the throat of the user 210 to aid in preventing the airway from closing and/or narrowing during sleep. The respiratory therapy device 122 can include the display device 128, which can allow the user to interact with the respiratory therapy device 122. The respiratory therapy device 122 can also include the humidification tank 129, which stores the water used to humidify the pressurized air. The respiratory therapy device 122 can be positioned on a nightstand 240 that is directly adjacent to the bed 230 as shown in FIG. 2, or more generally, on any surface or structure that is generally adjacent to the bed 230 and/or the user 210. The user can also wear the blood pressure device 180 and the activity tracker 190 while lying on the mattress 232 in the bed 230.

Referring back to FIG. 1, the one or more sensors 130 of the system 100 include a pressure sensor 132, a flow rate sensor 134, temperature sensor 136, a motion sensor 138, a microphone 140, a speaker 142, a radio-frequency (RF) receiver 146, an RF transmitter 148, a camera 150, an infrared (IR) sensor 152, a photoplethysmogram (PPG) sensor 154, an electrocardiogram (ECG) sensor 156, an electroencephalography (EEG) sensor 158, a capacitive sensor 160, a force sensor 162, a strain gauge sensor 164, an electromyography (EMG) sensor 166, an oxygen sensor 168, an analyte sensor 174, a moisture sensor 176, a light detection and ranging (LiDAR) sensor 178, or any combination thereof. Generally, each of the one or sensors 130 are configured to output sensor data that is received and stored in the memory device 114 or one or more other memory devices. The sensors 130 can also include, an electrooculography (EOG) sensor, a peripheral oxygen saturation ($SpO_2$) sensor, a galvanic skin response (GSR) sensor, a carbon dioxide ($CO_2$) sensor, or any combination thereof.

While the one or more sensors 130 are shown and described as including each of the pressure sensor 132, the flow rate sensor 134, the temperature sensor 136, the motion sensor 138, the microphone 140, the speaker 142, the RF receiver 146, the RF transmitter 148, the camera 150, the IR sensor 152, the PPG sensor 154, the ECG sensor 156, the EEG sensor 158, the capacitive sensor 160, the force sensor 162, the strain gauge sensor 164, the EMG sensor 166, the oxygen sensor 168, the analyte sensor 174, the moisture sensor 176, and the LiDAR sensor 178, more generally, the one or more sensors 130 can include any combination and any number of each of the sensors described and/or shown herein.

The one or more sensors 130 can be used to generate, for example physiological data, acoustic data, or both, that is associated with a user of the respiratory therapy system 120 (such as the user 210 of FIG. 2), the respiratory therapy system 120, both the user and the respiratory therapy system 120, or other entities, objects, activities, etc. Physiological data generated by one or more of the sensors 130 can be used by the control system 110 to determine a sleep-wake signal associated with the user during the sleep session and one or more sleep-related parameters. The sleep-wake signal can be indicative of one or more sleep stages (sometimes referred to as sleep states), including sleep, wakefulness, relaxed wakefulness, micro-awakenings, or distinct sleep stages such as a rapid eye movement (REM) stage (which can include both a typical REM stage and an atypical REM stage), a first non-REM stage (often referred to as "N1"), a second non-REM stage (often referred to as "N2"), a third non-REM stage (often referred to as "N3"), or any combination thereof. Methods for determining sleep stages from physiological data generated by one or more of the sensors, such as sensors 130, are described in, for example, WO 2014/047310, U.S. Pat. Nos. 10,492,720, 10,660,563, US 2020/0337634, WO 2017/132726, WO 2019/122413, US 2021/0150873, WO 2019/122414, US 2020/0383580, each of which is hereby incorporated by reference herein in its entirety.

The sleep-wake signal can also be timestamped to indicate a time that the user enters the bed, a time that the user exits the bed, a time that the user attempts to fall asleep, etc. The sleep-wake signal can be measured one or more of the sensors 130 during the sleep session at a predetermined sampling rate, such as, for example, one sample per second, one sample per seconds, one sample per minute, etc. Examples of the one or more sleep-related parameters that can be determined for the user during the sleep session based at least in part on the sleep-wake signal include a total time in bed, a total sleep time, a total wake time, a sleep onset latency, a wake-after-sleep-onset parameter, a sleep efficiency, a fragmentation index, an amount of time to fall asleep, a consistency of breathing rate, a fall asleep time, a wake time, a rate of sleep disturbances, a number of movements, or any combination thereof.

Physiological data and/or acoustic data generated by the one or more sensors 130 can also be used to determine a respiration signal associated with the user during a sleep session. The respiration signal is generally indicative of respiration or breathing of the user during the sleep session. The respiration signal can be indicative of, for example, a respiration rate, a respiration rate variability, an inspiration amplitude, an expiration amplitude, an inspiration-expiration amplitude ratio, an inspiration-expiration duration ratio, a number of events per hour, a pattern of events, pressure settings of the respiratory therapy device 122, or any combination thereof. The event(s) can include snoring, apneas, central apneas, obstructive apneas, mixed apneas, hypopneas, RERAs, a flow limitation (e.g., an event that results in the absence of the increase in flow despite an elevation in negative intrathoracic pressure indicating increased effort), a mask leak (e.g., from the user interface 124), a restless leg, a sleeping disorder, choking, an increased heart rate, a heart rate variation, labored breathing, an asthma attack, an epileptic episode, a seizure, a fever, a cough, a sneeze, a snore, a gasp, the presence of an illness such as the common cold or the flu, an elevated stress level, etc. Events can be detected by any means known in the art such as described in, for example, U.S. Pat. Nos. 5,245,995, 6,502,572, WO 2018/050913, WO 2020/104465, each of which is incorporated by reference herein in its entirety.

The pressure sensor 132 outputs pressure data that can be stored in the memory device 114 and/or analyzed by the processor 112 of the control system 110. In some implementations, the pressure sensor 132 is an air pressure sensor (e.g., barometric pressure sensor) that generates sensor data indicative of the respiration (e.g., inhaling and/or exhaling) of the user of the respiratory therapy system 120 and/or ambient pressure. In such implementations, the pressure sensor 132 can be coupled to or integrated in the respiratory therapy device 122. The pressure sensor 132 can be, for example, a capacitive sensor, an electromagnetic sensor, an inductive sensor, a resistive sensor, a piezoelectric sensor, a strain-gauge sensor, an optical sensor, a potentiometric sensor, or any combination thereof. In one example, the pressure sensor 132 can be used to determine a blood pressure of the user.

The flow rate sensor 134 outputs flow rate data that can be stored in the memory device 114 and/or analyzed by the processor 112 of the control system 110. In some implementations, the flow rate sensor 134 is used to determine an air flow rate from the respiratory therapy device 122, an air flow rate through the conduit 126, an air flow rate through the user interface 124, or any combination thereof. In such implementations, the flow rate sensor 134 can be coupled to or integrated in the respiratory therapy device 122, the user interface 124, or the conduit 126. The flow rate sensor 134 can be a mass flow rate sensor such as, for example, a rotary flow meter (e.g., Hall effect flow meters), a turbine flow meter, an orifice flow meter, an ultrasonic flow meter, a hot wire sensor, a vortex sensor, a membrane sensor, or any combination thereof.

The temperature sensor 136 outputs temperature data that can be stored in the memory device 114 and/or analyzed by the processor 112 of the control system 110. In some implementations, the temperature sensor 136 generates temperatures data indicative of a core body temperature of the user, a skin temperature of the user 210, a temperature of the air flowing from the respiratory therapy device 122 and/or through the conduit 126, a temperature in the user interface 124, an ambient temperature, or any combination thereof. The temperature sensor 136 can be, for example, a thermocouple sensor, a thermistor sensor, a silicon band gap temperature sensor or semiconductor-based sensor, a resistance temperature detector, or any combination thereof.

The motion sensor 138 outputs motion data that can be stored in the memory device 114 and/or analyzed by the processor 112 of the control system 110. The motion sensor 138 can be used to detect movement of the user during the sleep session, and/or detect movement of any of the components of the respiratory therapy system 120, such as the respiratory therapy device 122, the user interface 124, or the conduit 126. The motion sensor 138 can include one or more inertial sensors, such as accelerometers, gyroscopes, and magnetometers. The motion sensor 138 can be used to detect motion or acceleration associated with arterial pulses, such as pulses in or around the face of the user and proximal to the user interface 124, and configured to detect features of the pulse shape, speed, amplitude, or volume. In some implementations, the motion sensor 138 alternatively or additionally generates one or more signals representing bodily movement of the user, from which may be obtained a signal representing a sleep state of the user; for example, via a respiratory movement of the user.

The microphone 140 outputs acoustic data that can be stored in the memory device 114 and/or analyzed by the processor 112 of the control system 110. The acoustic data generated by the microphone 140 is reproducible as one or more sound(s) during a sleep session (e.g., sounds from the user) to determine (e.g., using the control system 110) one or more sleep-related parameters, as described in further detail herein. The acoustic data from the microphone 140 can also be used to identify (e.g., using the control system 110) an event experienced by the user during the sleep session, as described in further detail herein. In other implementations, the acoustic data from the microphone 140 is representative of noise associated with the respiratory therapy system 120. In some implementations, the acoustic data from the microphone 140 can be analyzed to detect the presence of liquid in the respiratory therapy system 120, in particular in the user interface 124 and/or the conduit 126, as explained in further detail herein. In some implementations, the system 100 includes a plurality of microphones (e.g., two or more microphones and/or an array of microphones with beamforming) such that sound data generated by each of the plurality of microphones can be used to discriminate the sound data generated by another of the plurality of microphones. The microphone 140 can be coupled to or integrated in the respiratory therapy system 120 (or the system 100) generally in any configuration. For example, the microphone 140 can be disposed inside the respiratory therapy device 122, the user interface 124, the conduit 126, or other components. The microphone 140 can also be positioned adjacent to or coupled to the outside of the respiratory therapy device 122, the outside of the user interface 124, the outside of the conduit 126, or outside of any other components. The microphone 140 could also be a component of the user device 170 (e.g., the microphone 140 is a microphone of a smart phone). The microphone 140 can be integrated into the user interface 124, the conduit 126, the respiratory therapy device 122, or any combination thereof. In general, the microphone 140 can be located at any point within or adjacent to the air pathway of the respiratory therapy system 120, which includes at least the motor of the respiratory therapy device 122, the user interface 124, and the conduit 126. Thus, the air pathway can also be referred to as the acoustic pathway.

The speaker 142 outputs sound waves that are typically audible to the user. In one or more implementations, the sound waves can be audible to a user of the system 100 or inaudible to the user of the system (e.g., ultrasonic sound waves). The speaker 142 can be used, for example, as an alarm clock or to play an alert or message to the user (e.g., in response to an event). In some implementations, the speaker 142 can be used to communicate the acoustic data generated by the microphone 140 to the user. The speaker 142 can be coupled to or integrated in the respiratory therapy device 122, the user interface 124, the conduit 126, or the user device 170.

The microphone 140 and the speaker 142 can be used as separate devices. In some implementations, the microphone 140 and the speaker 142 can be combined into an acoustic sensor 141 (e.g., a SONAR sensor), as described in, for example, WO 2018/050913 and WO 2020/104465, each of which is hereby incorporated by reference herein in its entirety. In such implementations, the speaker 142 generates or emits sound waves at a predetermined interval and/or frequency, and the microphone 140 detects the reflections of the emitted sound waves from the speaker 142. The sound waves generated or emitted by the speaker 142 have a frequency that is not audible to the human ear (e.g., below 20 Hz or above around 18 kHz) so as not to disturb the sleep of the user or a bed partner of the user (such as bed partner 220 in FIG. 2). Based at least in part on the data from the microphone 140 and/or the speaker 142, the control system 110 can determine a location of the user and/or one or more of the sleep-related parameters described in herein, such as, for example, a respiration signal, a respiration rate, an inspiration amplitude, an expiration amplitude, an inspiration-expiration ratio, a number of events per hour, a pattern of events, a sleep stage, pressure settings of the respiratory therapy device 122, a mouth leak status, or any combination thereof. In this context, a SONAR sensor may be understood to concern an active acoustic sensing, such as by generating/transmitting ultrasound or low frequency ultrasound sensing signals (e.g., in a frequency range of about 17-23 kHz, 18-22 kHz, or 17-18 kHz, for example), through the air. Such a system may be considered in relation to WO 2018/050913 and WO 2020/104465 mentioned above. In some implementations, the speaker 142 is a bone conduction speaker. In some implementations, the one or more sensors 130 include (i) a first microphone that is the same or similar to the microphone 140, and is integrated into the acoustic sensor 141 and (ii) a second microphone that is the same as or similar to the microphone 140, but is separate and distinct from the first microphone that is integrated into the acoustic sensor 141.

The RF transmitter 148 generates and/or emits radio waves having a predetermined frequency and/or a predetermined amplitude (e.g., within a high frequency band, within a low frequency band, long wave signals, short wave signals, etc.). The RF receiver 146 detects the reflections of the radio waves emitted from the RF transmitter 148, and this data can be analyzed by the control system 110 to determine a location of the user and/or one or more of the sleep-related parameters described herein. An RF receiver (either the RF receiver 146 and the RF transmitter 148 or another RF pair) can also be used for wireless communication between the control system 110, the respiratory therapy device 122, the one or more sensors 130, the user device 170, or any combination thereof. While the RF receiver 146 and RF transmitter 148 are shown as being separate and distinct elements in FIG. 1, in some implementations, the RF receiver 146 and RF transmitter 148 are combined as a part of an RF sensor 147 (e.g., a RADAR sensor). In some such implementations, the RF sensor 147 includes a control circuit. The specific format of the RF communication could be WiFi, Bluetooth, etc.

In some implementations, the RF sensor 147 is a part of a mesh system. One example of a mesh system is a WiFi mesh system, which can include mesh nodes, mesh router(s), and mesh gateway(s), each of which can be mobile/movable or fixed. In such implementations, the WiFi mesh system includes a WiFi router and/or a WiFi controller and one or more satellites (e.g., access points), each of which include an RF sensor that the is the same as, or similar to, the RF sensor 147. The WiFi router and satellites continuously communicate with one another using WiFi signals. The WiFi mesh system can be used to generate motion data based at least in part on changes in the WiFi signals (e.g., differences in received signal strength) between the router and the satellite(s) due to an object or person moving partially obstructing the signals. The motion data can be indicative of motion, breathing, heart rate, gait, falls, behavior, etc., or any combination thereof.

The camera 150 outputs image data reproducible as one or more images (e.g., still images, video images, thermal images, or a combination thereof) that can be stored in the memory device 114. The image data from the camera 150 can be used by the control system 110 to determine one or more of the sleep-related parameters described herein. For example, the image data from the camera 150 can be used to identify a location of the user, to determine a time when the user enters the user's bed (such as bed 230 in FIG. 2), and to determine a time when the user exits the bed 230. The camera 150 can also be used to track eye movements, pupil dilation (if one or both of the user's eyes are open), blink rate, or any changes during REM sleep. The camera 150 can also be used to track the position of the user, which can impact the duration and/or severity of apneic episodes in users with positional obstructive sleep apnea.

The IR sensor 152 outputs infrared image data reproducible as one or more infrared images (e.g., still images, video images, or both) that can be stored in the memory device 114. The infrared data from the IR sensor 152 can be used to determine one or more sleep-related parameters during the sleep session, including a temperature of the user and/or movement of the user. The IR sensor 152 can also be used in conjunction with the camera 150 when measuring the presence, location, and/or movement of the user. The IR sensor 152 can detect infrared light having a wavelength between about 700 nm and about 1 mm, for example, while the camera 150 can detect visible light having a wavelength between about 380 nm and about 740 nm.

The IR sensor 152 outputs infrared image data reproducible as one or more infrared images (e.g., still images, video images, or both) that can be stored in the memory device 114. The infrared data from the IR sensor 152 can be used to determine one or more sleep-related parameters during the sleep session, including a temperature of the user and/or movement of the user. The IR sensor 152 can also be used in conjunction with the camera 150 when measuring the presence, location, and/or movement of the user. The IR sensor 152 can detect infrared light having a wavelength between about 700 nm and about 1 mm, for example, while the camera 150 can detect visible light having a wavelength between about 380 nm and about 740 nm.

The PPG sensor 154 outputs physiological data associated with the user that can be used to determine one or more sleep-related parameters, such as, for example, a heart rate, a heart rate pattern, a heart rate variability, a cardiac cycle, respiration rate, an inspiration amplitude, an expiration amplitude, an inspiration-expiration ratio, estimated blood pressure parameter(s), or any combination thereof. The PPG sensor 154 can be worn by the user, embedded in clothing and/or fabric that is worn by the user, embedded in and/or coupled to the user interface 124 and/or its associated headgear (e.g., straps, etc.), etc.

The ECG sensor 156 outputs physiological data associated with electrical activity of the heart of the user. In some implementations, the ECG sensor 156 includes one or more electrodes that are positioned on or around a portion of the user during the sleep session. The physiological data from the ECG sensor 156 can be used, for example, to determine one or more of the sleep-related parameters described herein.

The EEG sensor 158 outputs physiological data associated with electrical activity of the brain of the user. In some implementations, the EEG sensor 158 includes one or more electrodes that are positioned on or around the scalp of the user during the sleep session. The physiological data from the EEG sensor 158 can be used, for example, to determine a sleep stage of the user at any given time during the sleep session. In some implementations, the EEG sensor 158 can be integrated in the user interface 124 and/or the associated headgear (e.g., straps, etc.).

The capacitive sensor 160, the force sensor 162, and the strain gauge sensor 164 output data that can be stored in the memory device 114 and used by the control system 110 to determine one or more of the sleep-related parameters described herein. The EMG sensor 166 outputs physiological data associated with electrical activity produced by one or more muscles. The oxygen sensor 168 outputs oxygen data indicative of an oxygen concentration of gas (e.g., in the conduit 126 or at the user interface 124). The oxygen sensor 168 can be, for example, an ultrasonic oxygen sensor, an electrical oxygen sensor, a chemical oxygen sensor, an optical oxygen sensor, or any combination thereof. In some implementations, the one or more sensors 130 also include a galvanic skin response (GSR) sensor, a blood flow sensor, a respiration sensor, a pulse sensor, a sphygmomanometer sensor, an oximetry sensor, or any combination thereof.

The analyte sensor 174 can be used to detect the presence of an analyte in the exhaled breath of the user. The data output by the analyte sensor 174 can be stored in the memory device 114 and used by the control system 110 to determine the identity and concentration of any analytes in the user's breath. In some implementations, the analyte sensor 174 is positioned near a mouth of the user to detect analytes in breath exhaled from the user's mouth. For example, when the user interface 124 is a facial mask that covers the nose and mouth of the user, the analyte sensor 174 can be positioned within the facial mask to monitor the user mouth breathing. In other implementations, such as when the user interface 124 is a nasal mask or a nasal pillow mask, the analyte sensor 174 can be positioned near the nose of the user to detect analytes in breath exhaled through the user's nose. In still other implementations, the analyte sensor 174 can be positioned near the user's mouth when the user interface 124 is a nasal mask or a nasal pillow mask. In this implementation, the analyte sensor 174 can be used to detect whether any air is inadvertently leaking from the user's mouth. In some implementations, the analyte sensor 174 is a volatile organic compound (VOC) sensor that can be used to detect carbon-based chemicals or compounds, such as carbon dioxide. In some implementations, the analyte sensor 174 can also be used to detect whether the user is breathing through their nose or mouth. For example, if the data output by an analyte sensor 174 positioned near the mouth of the user or within the facial mask (in implementations where the user interface 124 is a facial mask) detects the presence of an analyte, the control system 110 can use this data as an indication that the user is breathing through their mouth.

The moisture sensor 176 outputs data that can be stored in the memory device 114 and used by the control system 110. The moisture sensor 176 can be used to detect moisture in various areas surrounding the user (e.g., inside the conduit 126 or the user interface 124, near the user's face, near the connection between the conduit 126 and the user interface 124, near the connection between the conduit 126 and the respiratory therapy device 122, etc.). Thus, in some implementations, the moisture sensor 176 can be coupled to or integrated into the user interface 124 or in the conduit 126 to monitor the humidity of the pressurized air from the respiratory therapy device 122. In other implementations, the moisture sensor 176 is placed near any area where moisture levels need to be monitored. The moisture sensor 176 can also be used to monitor the humidity of the ambient environment surrounding the user, for example the air inside the user's bedroom. The moisture sensor 176 can also be used to track the user's biometric response to environmental changes.

One or more LiDAR sensors 178 can be used for depth sensing. This type of optical sensor (e.g., laser sensor) can be used to detect objects and build three dimensional (3D) maps of the surroundings, such as of a living space. LiDAR can generally utilize a pulsed laser to make time of flight measurements. LiDAR is also referred to as 3D laser scanning. In an example of use of such a sensor, a fixed or mobile device (such as a smartphone) having a LiDAR sensor 178 can measure and map an area extending 5 meters or more away from the sensor. The LiDAR data can be fused with point cloud data estimated by an electromagnetic RADAR sensor, for example. The LiDAR sensor 178 may also use artificial intelligence (AI) to automatically geofence RADAR systems by detecting and classifying features in a space that might cause issues for RADAR systems, such a glass windows (which can be highly reflective to RADAR). LiDAR can also be used to provide an estimate of the height of a person, as well as changes in height when the person sits down, or falls down, for example. LiDAR may be used to form a 3D mesh representation of an environment. In a further use, for solid surfaces through which radio waves pass (e.g., radio-translucent materials), the LiDAR may reflect off such surfaces, thus allowing a classification of different type of obstacles.

While shown separately in FIG. 1, any combination of the one or more sensors 130 can be integrated in and/or coupled to any one or more of the components of the system 100, including the respiratory therapy device 122, the user interface 124, the conduit 126, the humidification tank 129, the control system 110, the user device 170, or any combination thereof. For example, the acoustic sensor 141 and/or the RF sensor 147 can be integrated in and/or coupled to the user device 170. In such implementations, the user device 170 can be considered a secondary device that generates additional or secondary data for use by the system 100 (e.g., the control system 110) according to some aspects of the present disclosure. In some implementations, the pressure sensor 132 and/or the flow rate sensor 134 are integrated into and/or coupled to the respiratory therapy device 122. In some implementations, at least one of the one or more sensors 130 is not coupled to the respiratory therapy device 122, the control system 110, or the user device 170, and is positioned generally adjacent to the user during the sleep session (e.g., positioned on or in contact with a portion of the user, worn by the user, coupled to or positioned on the nightstand, coupled to the mattress, coupled to the ceiling, etc.). More generally, the one or more sensors 130 can be positioned at any suitable location relative to the user such that the one or more sensors 130 can generate physiological data associated with the user and/or the bed partner 220 during one or more sleep session.

The data from the one or more sensors 130 can be analyzed to determine one or more sleep-related parameters, which can include a respiration signal, a respiration rate, a respiration pattern, an inspiration amplitude, an expiration amplitude, an inspiration-expiration ratio, an occurrence of one or more events, a number of events per hour, a pattern of events, an average duration of events, a range of event durations, a ratio between the number of different events, a sleep stage, an apnea-hypopnea index (AHI), or any combination thereof. The one or more events can include snoring, apneas, central apneas, obstructive apneas, mixed apneas, hypopneas, an intentional user interface leak, an unintentional user interface leak, a mouth leak, a cough, a restless leg, a sleeping disorder, choking, an increased heart rate, labored breathing, an asthma attack, an epileptic episode, a seizure, increased blood pressure, hyperventilation, or any combination thereof. Many of these sleep-related parameters are physiological parameters, although some of the sleep-related parameters can be considered to be non-physiological parameters. Other types of physiological and non-physiological parameters can also be determined, either from the data from the one or more sensors 130, or from other types of data.

The user device 170 includes a display device 172. The user device 170 can be, for example, a mobile device such as a smart phone, a tablet, a laptop, a gaming console, a smart watch, or the like. Alternatively, the user device 170 can be an external sensing system, a television (e.g., a smart television) or another smart home device (e.g., a smart speaker(s) such as Google Home®, Google Nest®, Amazon Echo®, Amazon Echo Show®, Alexa®-enabled devices, etc.). In some implementations, the user device 170 is a wearable device (e.g., a smart watch). The display device 172 is generally used to display image(s) including still images, video images, or both. In some implementations, the display device 172 acts as a human-machine interface (HMI) that includes a graphic user interface (GUI) configured to display the image(s) and an input interface. The display device 172 can be an LED display, an OLED display, an LCD display, or the like. The input interface can be, for example, a touchscreen or touch-sensitive substrate, a mouse, a keyboard, or any sensor system configured to sense inputs made by a human user interacting with the user device 170. In some implementations, one or more user devices 170 can be used by and/or included in the system 100.

The blood pressure device 180 is generally used to aid in generating physiological data for determining one or more blood pressure measurements associated with a user. The blood pressure device 180 can include at least one of the one or more sensors 130 to measure, for example, a systolic blood pressure component and/or a diastolic blood pressure component.

In some implementations, the blood pressure device 180 is a sphygmomanometer including an inflatable cuff that can be worn by a user and a pressure sensor (e.g., the pressure sensor 132 described herein). For example, as shown in the example of FIG. 2, the blood pressure device 180 can be worn on an upper arm of the user. In such implementations where the blood pressure device 180 is a sphygmomanometer, the blood pressure device 180 also includes a pump (e.g., a manually operated bulb) for inflating the cuff. In some implementations, the blood pressure device 180 is coupled to the respiratory therapy device 122 of the respiratory therapy system 120, which in turn delivers pressurized air to inflate the cuff. More generally, the blood pressure device 180 can be communicatively coupled with, and/or physically integrated in (e.g., within a housing), the control system 110, the memory device 114, the respiratory therapy system 120, the user device 170, and/or the activity tracker 190.

The activity tracker 190 is generally used to aid in generating physiological data for determining an activity measurement associated with the user. The activity measurement can include, for example, a number of steps, a distance traveled, a number of steps climbed, a duration of physical activity, a type of physical activity, an intensity of physical activity, time spent standing, a respiration rate, an average respiration rate, a resting respiration rate, a maximum respiration rate, a respiration rate variability, a heart rate, an average heart rate, a resting heart rate, a maximum heart rate, a heart rate variability, a number of calories burned, blood oxygen saturation, electrodermal activity (also known as skin conductance or galvanic skin response), or any combination thereof. The activity tracker 190 includes one or more of the sensors 130 described herein, such as, for example, the motion sensor 138 (e.g., one or more accelerometers and/or gyroscopes), the PPG sensor 154, and/or the ECG sensor 156.

In some implementations, the activity tracker 190 is a wearable device that can be worn by the user, such as a smartwatch, a wristband, a ring, or a patch. For example, referring to FIG. 2, the activity tracker 190 is worn on a wrist of the user. The activity tracker 190 can also be coupled to or integrated a garment or clothing that is worn by the user. Alternatively, still, the activity tracker 190 can also be coupled to or integrated in (e.g., within the same housing) the user device 170. More generally, the activity tracker 190 can be communicatively coupled with, or physically integrated in (e.g., within a housing), the control system 110, the memory device 114, the respiratory therapy system 120, the user device 170, and/or the blood pressure device 180.

While the control system 110 and the memory device 114 are described and shown in FIG. 1 as being a separate and distinct component of the system 100, in some implementations, the control system 110 and/or the memory device 114 are integrated in the user device 170 and/or the respiratory therapy device 122. Alternatively, in some implementations, the control system 110 or a portion thereof (e.g., the processor 112) can be located in a cloud (e.g., integrated in a server, integrated in an Internet of Things (IoT) device, connected to the cloud, be subject to edge cloud processing, etc.), located in one or more servers (e.g., remote servers, local servers, etc., or any combination thereof.

While system 100 is shown as including all of the components described above, more or fewer components can be included in a system for determining a length of a conduit, according to implementations of the present disclosure. For example, a first alternative system includes the control system 110, the memory device 114, and at least one of the one or more sensors 130. As another example, a second alternative system includes the control system 110, the memory device 114, at least one of the one or more sensors 130, and the user device 170. As yet another example, a third alternative system includes the control system 110, the memory device 114, the respiratory therapy system 120, at least one of the one or more sensors 130, and the user device 170. As a further example, a fourth alternative system includes the control system 110, the memory device 114, the respiratory therapy system 120, at least one of the one or more sensors 130, the user device 170, and the blood pressure device 180 and/or activity tracker 190. Thus, various systems for modifying pressure settings can be formed using any portion or portions of the components shown and described herein and/or in combination with one or more other components.

Referring again to FIG. 2, in some implementations, the control system 110, the memory device 114, any of the one or more sensors 130, or a combination thereof can be located on and/or in any surface and/or structure that is generally adjacent to the bed 230 and/or the user 210. For example, in some implementations, at least one of the one or more sensors 130 can be located at a first position on and/or in one or more components of the respiratory therapy system 120 adjacent to the bed 230 and/or the user 210. The one or more sensors 130 can be coupled to the respiratory therapy system 120, the user interface 124, the conduit 126, the display device 128, the humidification tank 129, or a combination thereof.

Alternatively, or additionally, at least one of the one or more sensors 130 can be located at a second position on and/or in the bed 230 (e.g., the one or more sensors 130 are coupled to and/or integrated in the bed 230). Further, alternatively or additionally, at least one of the one or more sensors 130 can be located at a third position on and/or in the mattress 232 that is adjacent to the bed 230 and/or the user 210 (e.g., the one or more sensors 130 are coupled to and/or integrated in the mattress 232). Alternatively, or additionally, at least one of the one or more sensors 130 can be located at a fourth position on and/or in a pillow that is generally adjacent to the bed 230 and/or the user 210.

Alternatively, or additionally, at least one of the one or more sensors 130 can be located at a fifth position on and/or in the nightstand 240 that is generally adjacent to the bed 230 and/or the user 210. Alternatively, or additionally, at least one of the one or more sensors 130 can be located at a sixth position such that the at least one of the one or more sensors 130 are coupled to and/or positioned on the user 210 (e.g., the one or more sensors 130 are embedded in or coupled to fabric, clothing, and/or a smart device worn by the user 210). More generally, at least one of the one or more sensors 130 can be positioned at any suitable location relative to the user 210 such that the one or more sensors 130 can generate sensor data associated with the user 210.

In some implementations, a primary sensor, such as the microphone 140, is configured to generate acoustic data associated with the user 210 during a sleep session. The acoustic data can be based on, for example, acoustic signals in the conduit 126 of the respiratory therapy system 120. For example, one or more microphones (the same as, or similar to, the microphone 140 of FIG. 1) can be integrated in and/or coupled to (i) a circuit board of the respiratory therapy device 122, (ii) the conduit 126, (iii) a connector between components of the respiratory therapy system 120, (iv) the user interface 124, (v) a headgear (e.g., straps) associated with the user interface, or (vi) a combination thereof. In some implementations, the microphone 140 is in fluid communication with the airflow pathway (e.g., an airflow pathway between the flow generator/motor and the distal end of the conduit). By fluid communication, it is intended to also include configurations wherein the microphone is in acoustic communication with the airflow pathway without being in direct or physical contact with the airflow. For example, in some implementations, the microphone is positioned on a circuit board and in fluid communication, optionally via a duct sealed by a membrane, to the airflow pathway.

In some implementations, one or more secondary sensors may be used in addition to the primary sensor to generate additional data. In some such implementations, the one or more secondary sensors include: a microphone (e.g., the microphone 140 of the system 100), a flow rate sensor (e.g., the flow rate sensor 134 of the system 100), a pressure sensor (e.g., the pressure sensor 132 of the system 100), a temperature sensor (e.g., the temperature sensor 136 of the system 100), a camera (e.g., the camera 150 of the system 100), a vane sensor (VAF), a hot wire sensor (MAF), a cold wire sensor, a laminar flow sensor, an ultrasonic sensor, an inertial sensor, or a combination thereof.

Additionally, or alternatively, one or more microphones (the same as, or similar to, the microphone 140 of FIG. 1) can be integrated in and/or coupled to a co-located smart device, such as the user device 170, a TV, a watch (e.g., a mechanical watch or another smart device worn by the user), a pendant, the mattress 232, the bed 230, beddings positioned on the bed 230, the pillow, a speaker (e.g., the speaker 142 of FIG. 1), a radio, a tablet device, a waterless humidifier, or a combination thereof. A co-located smart device can be any smart device that is within range for detecting sounds emitted by the user, the respiratory therapy system 120, and/or any portion of the system 100. In some implementations, the co-located smart device is a smart device that is in the same room as the user during the sleep session.

Additionally, or alternatively, in some implementations, one or more microphones (the same as, or similar to, the microphone 140 of FIG. 1) can be remote from the system 100 (FIG. 1) and/or the user 210 (FIG. 2), so long as there is an air passage allowing acoustic signals to travel to the one or more microphones. For example, the one or more microphones can be in a different room from the room containing the system 100.

As used herein, a sleep session can be defined in a number of ways based at least in part on, for example, an initial start time and an end time. In some implementations, a sleep session is a duration where the user is asleep, that is, the sleep session has a start time and an end time, and during the sleep session, the user does not wake until the end time. That is, any period of the user being awake is not included in a sleep session. From this first definition of sleep session, if the user wakes ups and falls asleep multiple times in the same night, each of the sleep intervals separated by an awake interval is a sleep session.

Alternatively, in some implementations, a sleep session has a start time and an end time, and during the sleep session, the user can wake up, without the sleep session ending, so long as a continuous duration that the user is awake is below an awake duration threshold. The awake duration threshold can be defined as a percentage of a sleep session. The awake duration threshold can be, for example, about twenty percent of the sleep session, about fifteen percent of the sleep session duration, about ten percent of the sleep session duration, about five percent of the sleep session duration, about two percent of the sleep session duration, etc., or any other threshold percentage. In some implementations, the awake duration threshold is defined as a fixed amount of time, such as, for example, about one hour, about thirty minutes, about fifteen minutes, about ten minutes, about five minutes, about two minutes, etc., or any other amount of time.

In some implementations, a sleep session is defined as the entire time between the time in the evening at which the user first entered the bed, and the time the next morning when user last left the bed. Put another way, a sleep session can be defined as a period of time that begins on a first date (e.g., Monday, Jan. 6, 2020) at a first time (e.g., 10:00 PM), that can be referred to as the current evening, when the user first enters a bed with the intention of going to sleep (e.g., not if the user intends to first watch television or play with a smart phone before going to sleep, etc.), and ends on a second date (e.g., Tuesday, Jan. 7, 2020) at a second time (e.g., 7:00 AM), that can be referred to as the next morning, when the user first exits the bed with the intention of not going back to sleep that next morning.

In some implementations, the user can manually define the beginning of a sleep session and/or manually terminate a sleep session. For example, the user can select (e.g., by clicking or tapping) one or more user-selectable element that is displayed on the display device 172 of the user device 170 (FIG. 1) to manually initiate or terminate the sleep session.

Figure 3:
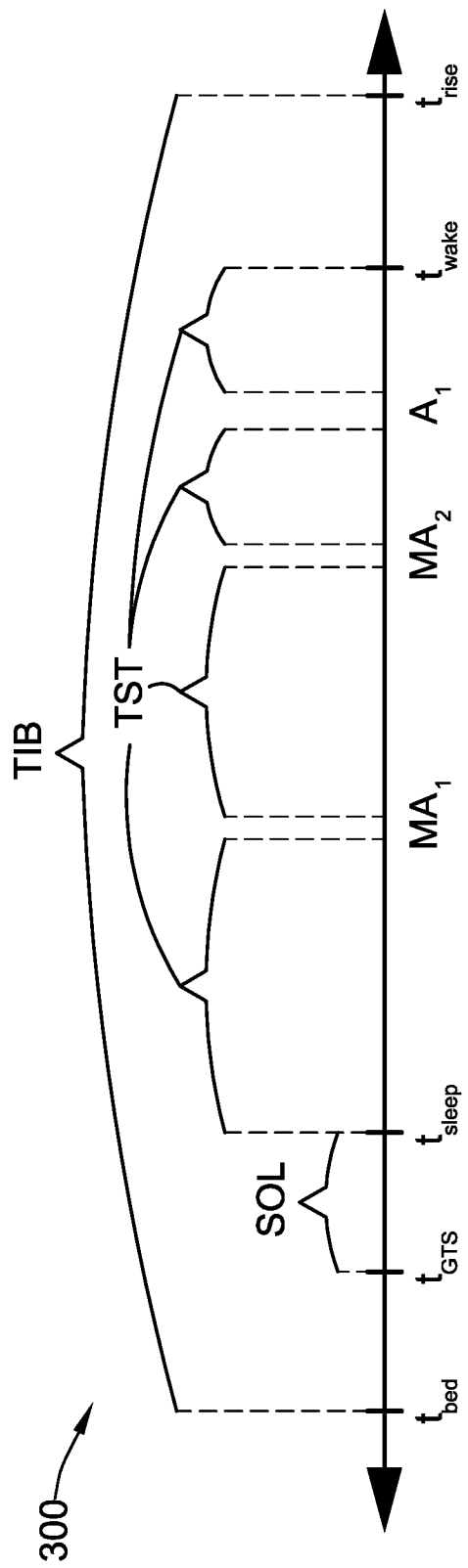
FIG. 3 illustrates an exemplary timeline for a sleep session, according to some implementations of the present disclosure.

Referring to FIG. 3, an exemplary timeline 300 for a sleep session is illustrated. The timeline 300 includes an enter bed time ($t_{bed}$), a go-to-sleep time ($t_{GTS}$), an initial sleep time ($t_{sleep}$), a first micro-awakening $MA_1$, a second micro-awakening $MA_2$, an awakening A, a wake-up time ($t_{wake}$), and a rising time ($t_{rise}$).

The enter bed time is associated with the time that the user initially enters the bed (e.g., bed 230 in FIG. 2) prior to falling asleep (e.g., when the user lies down or sits in the bed). The enter bed time $t_{bed}$ can be identified based at least in part on a bed threshold duration to distinguish between times when the user enters the bed for sleep and when the user enters the bed for other reasons (e.g., to watch TV). For example, the bed threshold duration can be at least about 10 minutes, at least about 20 minutes, at least about 30 minutes, at least about 45 minutes, at least about 1 hour, at least about 2 hours, etc. While the enter bed time $t_{bed}$ is described herein in reference to a bed, more generally, the enter time $t_{bed}$ can refer to the time the user initially enters any location for sleeping (e.g., a couch, a chair, a sleeping bag, etc.).

The go-to-sleep time (GTS) is associated with the time that the user initially attempts to fall asleep after entering the bed ($t_{bed}$). For example, after entering the bed, the user may engage in one or more activities to wind down prior to trying to sleep (e.g., reading, watching TV, listening to music, using the user device 170, etc.). The initial sleep time ($t_{sleep}$) is the time that the user initially falls asleep. For example, the initial sleep time ($t_{sleep}$) can be the time that the user initially enters the first non-REM sleep stage.

The wake-up time $t_{wake}$ is the time associated with the time when the user wakes up without going back to sleep (e.g., as opposed to the user waking up in the middle of the night and going back to sleep). The user may experience one of more unconscious microawakenings (e.g., microawakenings $MA_1$ and $MA_2$) having a short duration (e.g., 5 seconds, 10 seconds, seconds, 1 minute, etc.) after initially falling asleep. In contrast to the wake-up time $t_{wake}$, the user goes back to sleep after each of the microawakenings $MA_1$ and $MA_2$. Similarly, the user may have one or more conscious awakenings (e.g., awakening A) after initially falling asleep (e.g., getting up to go to the bathroom, attending to children or pets, sleep walking, etc.). However, the user goes back to sleep after the awakening A. Thus, the wake-up time $t_{wake}$ can be defined, for example, based at least in part on a wake threshold duration (e.g., the user is awake for at least 15 minutes, at least 20 minutes, at least 30 minutes, at least 1 hour, etc.).

Similarly, the rising time $t_{rise}$ is associated with the time when the user exits the bed and stays out of the bed with the intent to end the sleep session (e.g., as opposed to the user getting up during the night to go to the bathroom, to attend to children or pets, sleep walking, etc.). In other words, the rising time $t_{rise}$ is the time when the user last leaves the bed without returning to the bed until a next sleep session (e.g., the following evening). Thus, the rising time $t_{rise}$ can be defined, for example, based at least in part on a rise threshold duration (e.g., the user has left the bed for at least 15 minutes, at least 20 minutes, at least 30 minutes, at least 1 hour, etc.). The enter bed time $t_{bed}$ time for a second, subsequent sleep session can also be defined based at least in part on a rise threshold duration (e.g., the user has left the bed for at least 4 hours, at least 6 hours, at least 8 hours, at least 12 hours, etc.).

As described above, the user may wake up and get out of bed one more times during the night between the initial $t_{bed}$ and the final $t_{rise}$. In some implementations, the final wake-up time $t_{wake}$ and/or the final rising time $t_{rise}$ that are identified or determined based at least in part on a predetermined threshold duration of time subsequent to an event (e.g., falling asleep or leaving the bed). Such a threshold duration can be customized for the user. For a standard user which goes to bed in the evening, then wakes up and goes out of bed in the morning any period (between the user waking up ($t_{wake}$) or raising up ($t_{rise}$), and the user either going to bed ($t_{bed}$), going to sleep ($t_{GTS}$) or falling asleep ($t_{sleep}$) of between about 12 and about 18 hours can be used. For users that spend longer periods of time in bed, shorter threshold periods may be used (e.g., between about 8 hours and about 14 hours). The threshold period may be initially selected and/or later adjusted based at least in part on the system monitoring the user's sleep behavior.

The total time in bed (TIB) is the duration of time between the time enter bed time $t_{bed}$ and the rising time $t_{rise}$. The total sleep time (TST) is associated with the duration between the initial sleep time and the wake-up time, excluding any conscious or unconscious awakenings and/or micro-awakenings therebetween. Generally, the total sleep time (TST) will be shorter than the total time in bed (TIB) (e.g., one minute short, ten minutes shorter, one hour shorter, etc.). For example, referring to the timeline 300 of FIG. 3, the total sleep time (TST) spans between the initial sleep time $t_{sleep}$ and the wake-up time $t_{wake}$, but excludes the duration of the first micro-awakening $MA_1$, the second micro-awakening $MA_2$, and the awakening A. As shown, in this example, the total sleep time (TST) is shorter than the total time in bed (TIB).

In some implementations, the total sleep time (TST) can be defined as a persistent total sleep time (PTST). In such implementations, the persistent total sleep time excludes a predetermined initial portion or period of the first non-REM stage (e.g., light sleep stage). For example, the predetermined initial portion can be between about 30 seconds and about 20 minutes, between about 1 minute and about 10 minutes, between about 3 minutes and about 5 minutes, etc. The persistent total sleep time is a measure of sustained sleep, and smooths the sleep-wake hypnogram. For example, when the user is initially falling asleep, the user may be in the first non-REM stage for a very short time (e.g., about 30 seconds), then back into the wakefulness stage for a short period (e.g., one minute), and then goes back to the first non-REM stage. In this example, the persistent total sleep time excludes the first instance (e.g., about 30 seconds) of the first non-REM stage.

In some implementations, the sleep session is defined as starting at the enter bed time ($t_{bed}$) and ending at the rising time ($t_{rise}$), i.e., the sleep session is defined as the total time in bed (TIB). In some implementations, a sleep session is defined as starting at the initial sleep time ($t_{sleep}$) and ending at the wake-up time ($t_{wake}$). In some implementations, the sleep session is defined as the total sleep time (TST). In some implementations, a sleep session is defined as starting at the go-to-sleep time ($t_{GTS}$) and ending at the wake-up time ($t_{wake}$). In some implementations, a sleep session is defined as starting at the go-to-sleep time ($t_{GTS}$) and ending at the rising time ($t_{rise}$). In some implementations, a sleep session is defined as starting at the enter bed time ($t_{bed}$) and ending at the wake-up time ($t_{wake}$). In some implementations, a sleep session is defined as starting at the initial sleep time ($t_{sleep}$) and ending at the rising time ($t_{rise}$).

Figure 4:
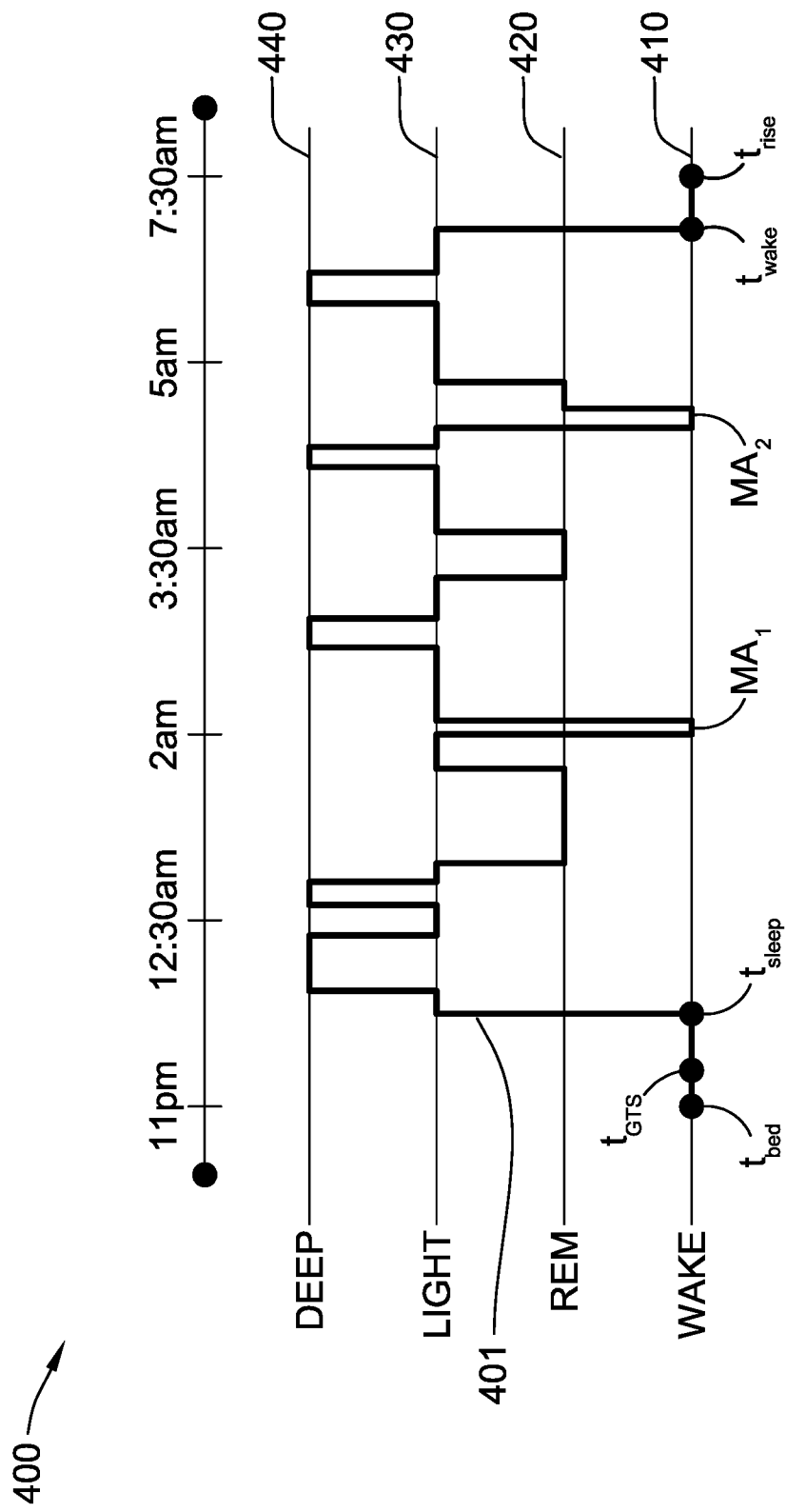
FIG. 4 illustrates an exemplary hypnogram associated with the sleep session of FIG. 3, according to some implementations of the present disclosure.

Referring to FIG. 4, an exemplary hypnogram 400 corresponding to the timeline 300 (FIG. 3), according to some implementations, is illustrated. As shown, the hypnogram 400 includes a sleep-wake signal 401, a wakefulness stage axis 410, a REM stage axis 420, a light sleep stage axis 430, and a deep sleep stage axis 440. The intersection between the sleep-wake signal 401 and one of the axes 410-440 is indicative of the sleep stage at any given time during the sleep session.

The sleep-wake signal 401 can be generated based at least in part on physiological data associated with the user (e.g., generated by one or more of the sensors 130 described herein). The sleep-wake signal can be indicative of one or more sleep stages, including wakefulness, relaxed wakefulness, microawakenings, a REM stage, a first non-REM stage, a second non-REM stage, a third non-REM stage, or any combination thereof. In some implementations, one or more of the first non-REM stage, the second non-REM stage, and the third non-REM stage can be grouped together and categorized as a light sleep stage or a deep sleep stage. For example, the light sleep stage can include the first non-REM stage and the deep sleep stage can include the second non-REM stage and the third non-REM stage. While the hypnogram 400 is shown in FIG. 4 as including the light sleep stage axis 430 and the deep sleep stage axis 440, in some implementations, the hypnogram 400 can include an axis for each of the first non-REM stage, the second non-REM stage, and the third non-REM stage. In other implementations, the sleep-wake signal can also be indicative of a respiration signal, a respiration rate, an inspiration amplitude, an expiration amplitude, an inspiration-expiration amplitude ratio, an inspiration-expiration duration ratio, a number of events per hour, a pattern of events, or any combination thereof. Information describing the sleep-wake signal can be stored in the memory device 114.

The hypnogram 400 can be used to determine one or more sleep-related parameters, such as, for example, a sleep onset latency (SOL), wake-after-sleep onset (WASO), a sleep efficiency (SE), a sleep fragmentation index, sleep blocks, or any combination thereof.

The sleep onset latency (SOL) is defined as the time between the go-to-sleep time ($t_{GTS}$) and the initial sleep time ($t_{sleep}$). In other words, the sleep onset latency is indicative of the time that it took the user to actually fall asleep after initially attempting to fall asleep. In some implementations, the sleep onset latency is defined as a persistent sleep onset latency (PSOL). The persistent sleep onset latency differs from the sleep onset latency in that the persistent sleep onset latency is defined as the duration time between the go-to-sleep time and a predetermined amount of sustained sleep. In some implementations, the predetermined amount of sustained sleep can include, for example, at least 10 minutes of sleep within the second non-REM stage, the third non-REM stage, and/or the REM stage with no more than 2 minutes of wakefulness, the first non-REM stage, and/or movement therebetween. In other words, the persistent sleep onset latency requires up to, for example, 8 minutes of sustained sleep within the second non-REM stage, the third non-REM stage, and/or the REM stage. In other implementations, the predetermined amount of sustained sleep can include at least 10 minutes of sleep within the first non-REM stage, the second non-REM stage, the third non-REM stage, and/or the REM stage subsequent to the initial sleep time. In such implementations, the predetermined amount of sustained sleep can exclude any micro-awakenings (e.g., a ten second micro-awakening does not restart the 10-minute period).

The wake-after-sleep onset (WASO) is associated with the total duration of time that the user is awake between the initial sleep time and the wake-up time. Thus, the wake-after-sleep onset includes short and micro-awakenings during the sleep session (e.g., the micro-awakenings $MA_1$ and $MA_2$ shown in FIG. 4), whether conscious or unconscious.

In some implementations, the wake-after-sleep onset (WASO) is defined as a persistent wake-after-sleep onset (PWASO) that only includes the total durations of awakenings having a predetermined length (e.g., greater than 10 seconds, greater than 30 seconds, greater than 60 seconds, greater than about 5 minutes, greater than about 10 minutes, etc.)

The sleep efficiency (SE) is determined as a ratio of the total time in bed (TIB) and the total sleep time (TST). For example, if the total time in bed is 8 hours and the total sleep time is 7.5 hours, the sleep efficiency for that sleep session is 93.75%. The sleep efficiency is indicative of the sleep hygiene of the user. For example, if the user enters the bed and spends time engaged in other activities (e.g., watching TV) before sleep, the sleep efficiency will be reduced (e.g., the user is penalized). In some implementations, the sleep efficiency (SE) can be calculated based at least in part on the total time in bed (TIB) and the total time that the user is attempting to sleep. In such implementations, the total time that the user is attempting to sleep is defined as the duration between the go-to-sleep (GTS) time and the rising time described herein. For example, if the total sleep time is 8 hours (e.g., between 11 PM and 7 AM), the go-to-sleep time is 10:45 PM, and the rising time is 7:15 AM, in such implementations, the sleep efficiency parameter is calculated as about 94%.

The fragmentation index is determined based at least in part on the number of awakenings during the sleep session. For example, if the user had two micro-awakenings (e.g., micro-awakening $MA_1$ and micro-awakening $MA_2$ shown in FIG. 4), the fragmentation index can be expressed as 2. In some implementations, the fragmentation index is scaled between a predetermined range of integers (e.g., between 0 and 10).

The sleep blocks are associated with a transition between any stage of sleep (e.g., the first non-REM stage, the second non-REM stage, the third non-REM stage, and/or the REM) and the wakefulness stage. The sleep blocks can be calculated at a resolution of, for example, seconds.

In some implementations, the systems and methods described herein can include generating or analyzing a hypnogram including a sleep-wake signal to determine or identify the enter bed time (teed), the go-to-sleep time ($t_{GTS}$), the initial sleep time ($t_{sleep}$), one or more first micro-awakenings (e.g., $MA_1$ and $MA_2$), the wake-up time ($t_{wake}$), the rising time ($t_{rise}$), or any combination thereof based at least in part on the sleep-wake signal of a hypnogram.

In other implementations, one or more of the sensors 130 can be used to determine or identify the enter bed time (teed), the go-to-sleep time ($t_{GTS}$), the initial sleep time ($t_{sleep}$), one or more first micro-awakenings (e.g., $MA_1$ and $MA_2$), the wake-up time ($t_{wake}$), the rising time ($t_{rise}$), or any combination thereof, which in turn define the sleep session. For example, the enter bed time teed can be determined based at least in part on, for example, data generated by the motion sensor 138, the microphone 140, the camera 150, or any combination thereof. The go-to-sleep time can be determined based at least in part on, for example, data from the motion sensor 138 (e.g., data indicative of no movement by the user), data from the camera 150 (e.g., data indicative of no movement by the user and/or that the user has turned off the lights), data from the microphone 140 (e.g., data indicative of the using turning off a TV), data from the user device 170 (e.g., data indicative of the user no longer using the user device 170), data from the pressure sensor 132 and/or the flow rate sensor 134 (e.g., data indicative of the user turning on the respiratory therapy device 122, data indicative of the user donning the user interface 124, etc.), or any combination thereof.

During use of the respiratory therapy system 120, liquid can accumulate in various components of the respiratory therapy system 120. For example, as discuss herein, the humidification tank 129 contains a reservoir of water that can be heated to vaporize the liquid water into a gas. The water vapor humidifies the pressurized air that passes through the humidification tank 129 into the conduit 126. If the humidified pressurized air cools, the water vapor can condense back into liquid form, such that the liquid water can accumulate within the conduit 126. The liquid water can also accumulate within the housing of the respiratory therapy device 122 and within the user interface 124. In some examples, if the user interface 124 contains material that can absorb liquid, this liquid water can saturate portions of the user interface 124. In yet another example, if the user overfills the humidification tank 129, excess liquid can spill from the humidification tank 129 into other parts of the respiratory therapy device 120. Other liquids may also accumulate within various portions of the respiratory therapy system 120.

Accumulation of liquid within the conduit 126 or other parts of the respiratory therapy system 120 is known as rainout. This accumulated liquid can disrupt the operation of the respiratory therapy system 120. For example, liquid accumulating in the conduit 126 can cause a gurgling noise during operation of the respiratory therapy system 120, as the pressurized air is directed through the conduit 126 to the user interface 124. This gurgling noise can wake up the user during the sleep session and/or prevent the user from falling asleep during the sleep session. The gurgling noise can also cause the user to experience anxiety, claustrophobia, etc. Liquid that accumulates in the user interface 124 or saturates liquid-absorbing portions of the user interface 124 can also cause unwanted noises, or contribute to feelings of anxiety and/or claustrophobia in the user.

Figure 5:
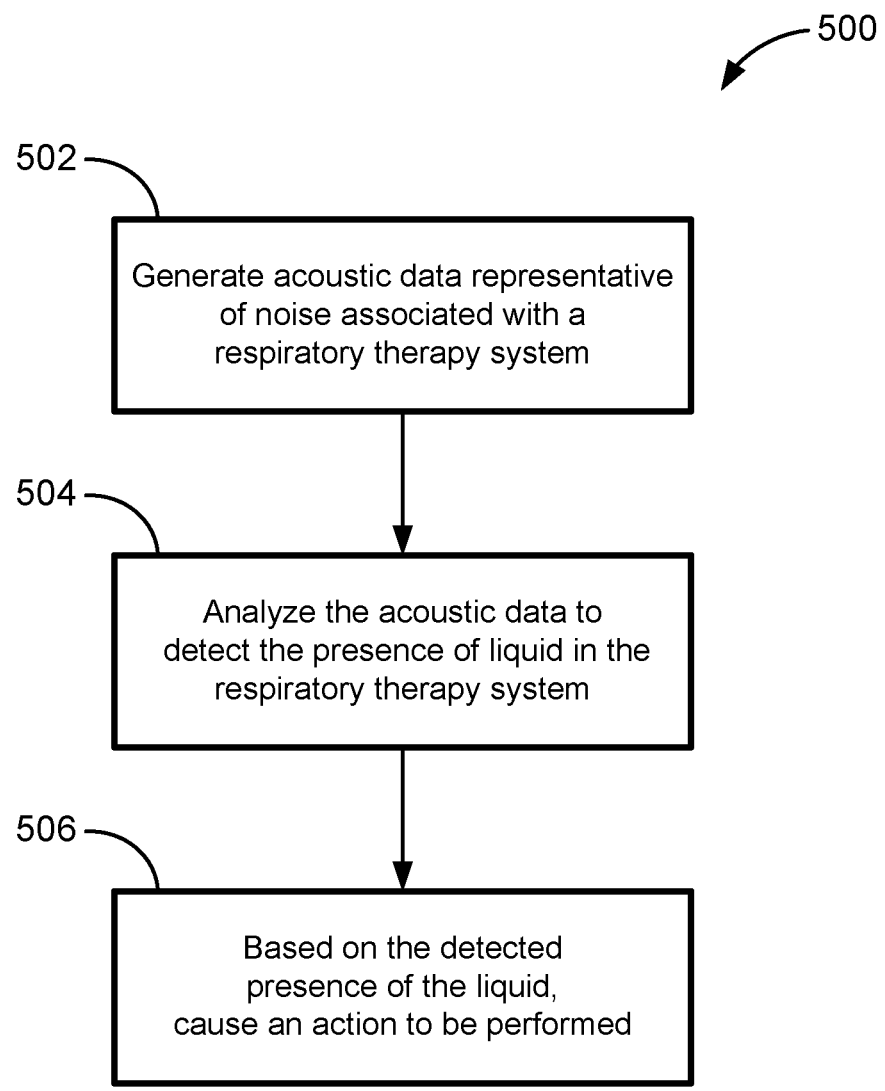
FIG. 5 illustrates a flow diagram of a process for detecting rainout in a respiratory therapy system, according to some implementations of the present disclosure.

FIG. 5 illustrates a method 500 for detecting rainout in a respiratory therapy system (such as respiratory therapy system 120) that includes a respiratory therapy device configured to supply pressurized air (such as respiratory therapy device 122), and a user interface (such as user interface 124) coupled to the respiratory therapy device via a conduit (such as conduit 126). The user interface is configured to engage with the user, and aids in directing the pressurized air to the user's airway. Generally, a control system having one or more processors (such as control system 110 of system 100) is configured to carry out the steps of method 500. A memory device (such as memory device 114 of system 100) can be used to store machine-readable instructions that are executed by the control system to carry out the steps of method 500. The memory device can also store any type of data utilized in the steps of method 500. Generally, method 500 can be implemented using a system (such as system 100) that includes the respiratory therapy system, the control system, and the memory device.

At step 502 of method 500, acoustic data is generated. In some implementations, the respiratory therapy system includes one or more microphones. Additionally or alternatively, one or more microphones may be part of the same larger system as the respiratory therapy system. The one or more microphones can be located at any location relative to the respiratory therapy system. For example, the respiratory therapy system may include a microphone located inside of or outside of the housing of the respiratory therapy device; inside of or outside of the user interface; inside of or outside of the conduit; on a circuit board of the respiratory therapy device; anywhere in the air pathway of the respiratory therapy system; or in any other suitable location. In some implementations, the one or more microphones include the microphone 140 as part of the acoustic sensor 141.

The acoustic data generated by the one or more microphones is representative of noise that may be occurring in the environment where the respiratory therapy system is located, e.g., the user's bedroom. This noise can include noise that is representative of or characteristic of liquid (if present) in the respiratory therapy system. For example, if any type of liquid is accumulating in the respiratory therapy system such that noise associated with (e.g., caused by) the liquid (e.g., a gurgling noise) is being produced, this noise can be detected by the microphone, and represented by the generated acoustic data. In these and other implementations, as discussed further herein, the acoustic data may be associated with a reflection of an acoustic signal that is emitted in order to measure physical characteristics of the conduit, or of other components of the respiratory therapy system. The acoustic signal may be emitted by, for example, a speaker, or may be generated as a result of the operation of the motor of the respiratory therapy device. In general, in order to detect rainout in the respiratory therapy system, the noise represented by the acoustic data is noise caused by the presence of liquid somewhere in the respiratory therapy system, such as, in particular, the conduit, the user interface, or the respiratory therapy device.

At step 504 of method 500, the acoustic data is analyzed to detect the presence of liquid in the respiratory therapy system. A variety of different techniques can be used to analyze the acoustic data. In some implementations, the noise caused by the presence of the liquid results in a specific acoustic pattern or acoustic signature in the acoustic data. Generally, an acoustic signature can be any feature or combination of features in the acoustic data that are caused by a certain type of noise. The acoustic signature is generally unique to the certain type of noise. An acoustic pattern could be any type of periodic (e.g., repeating) feature or features in the acoustic data that results from a certain type of noise. In some implementations, the acoustic pattern resulting from a certain type of noise is the acoustic signature of that noise. In other implementations, the acoustic pattern resulting from a certain type of noise may be shared between multiple types of noise. The acoustic data can be analyzed to identify this acoustic pattern or acoustic signature of the noise caused by the presence of the liquid.

One technique for analyzing the acoustic data includes generating time-domain measurements, such as a measurement representing the intensity of the detected noise (e.g., volume) versus time. The intensity of the noise can be analyzed to detect an acoustic pattern or acoustic signature indicative of noise caused by the presence of the liquid. In one example, liquid in the conduit may cause a gurgling sound, which is represented by a periodic intensity pattern in the time-domain measurement, e.g., a plot of the intensity of the detected noise versus time where the intensity repeatedly increases and decreases over time. The intensity may vary (e.g., increase and decrease, wax and wane, etc.) generally over a variety of different time periods, and still indicate a gurgling noise. In some cases, the intensity increases and decreases several times (e.g., two to five times) per second. This periodic intensity pattern can be identified to detect the presence of liquid in the conduit. Additionally or alternatively, a volume level of the noise caused by the presence of the liquid can be determined from a measurement representing the intensity of the noise versus time. If the volume reaches a sufficient threshold volume, it can be determined that there is liquid in the conduit, or in another component of the respiratory therapy system. In some implementations, the volume of the noise is compared to a baseline volume level. The baseline volume level can be determined by measuring the noise of the respiratory therapy system when it is known that there is no liquid within the conduit or other component. If the volume level of the detected noise exceeds the baseline volume level by a sufficient amount, it can be determined that there is liquid in the conduit.

Another technique for analyzing the acoustic data includes generating frequency-domain measurements, such as a frequency spectrum that represents the intensity of the detected noise versus frequency. In some implementations, the frequency spectrum can be obtained by taking the Fourier transform of the measurement representing the intensity of the detected noise versus time. The frequency spectrum can be analyzed to identify various features representing the noise caused by the presence of the liquid. For example, if liquid has accumulated within the conduit, the resulting noise may have a distinct frequency, or be composed of multiple frequencies within distinct frequency range. This frequency or frequency range can be identified from the frequency spectrum in order to determine that there is liquid within the conduit.

A further technique for analyzing the acoustic data includes utilizing cepstrum analysis. A cepstrum can be considered as a spectrum of a spectrum, and can be obtained in some implementations by taking the inverse Fourier Transform of the logarithm of the frequency spectrum. In some implementations, the frequency spectrum is plotted on the mel scale. The mel scale is a warped version of a linear frequency scale, where the difference between consecutive frequency intervals is not equally-spaced as the frequency increases. The mel scale generally approximates the response of the human auditory scale more accurately than a linear frequency scale. When utilizing a frequency spectrum plotted on the mel scale, a discrete cosine transform of the frequency spectrum can be taken (instead of the inverse Fourier Transform), to obtain a mel-frequency cepstrum. After the mel-frequency cepstrum has been generated, the mel-frequency cepstral coefficients can be determined from the mel-frequency cepstrum. The mel-frequency cepstral coefficients are the amplitudes of the components of the spectrum.

The mel-frequency cepstral coefficients can be correlated with different noises in order to detect when liquid within the conduit (or another component of the respiratory therapy system) is causing noise. In some implementations, a machine learning model (such as a convolutional neural network) can be trained to detect noise caused by the presence of the liquid. In these implementations, data representing mel-frequency cepstral coefficients known to result from the operation of the respiratory therapy system when liquid is present in the conduit (or another component of the respiratory therapy system) is input into the machine learning model as training data. Once the machine learning model has been sufficiently trained, the machine learning model can accurately determine whether new mel-frequency cepstral coefficients represent noise caused by the presence of liquid in the conduit or other component of the respiratory therapy system.

Figure 6:
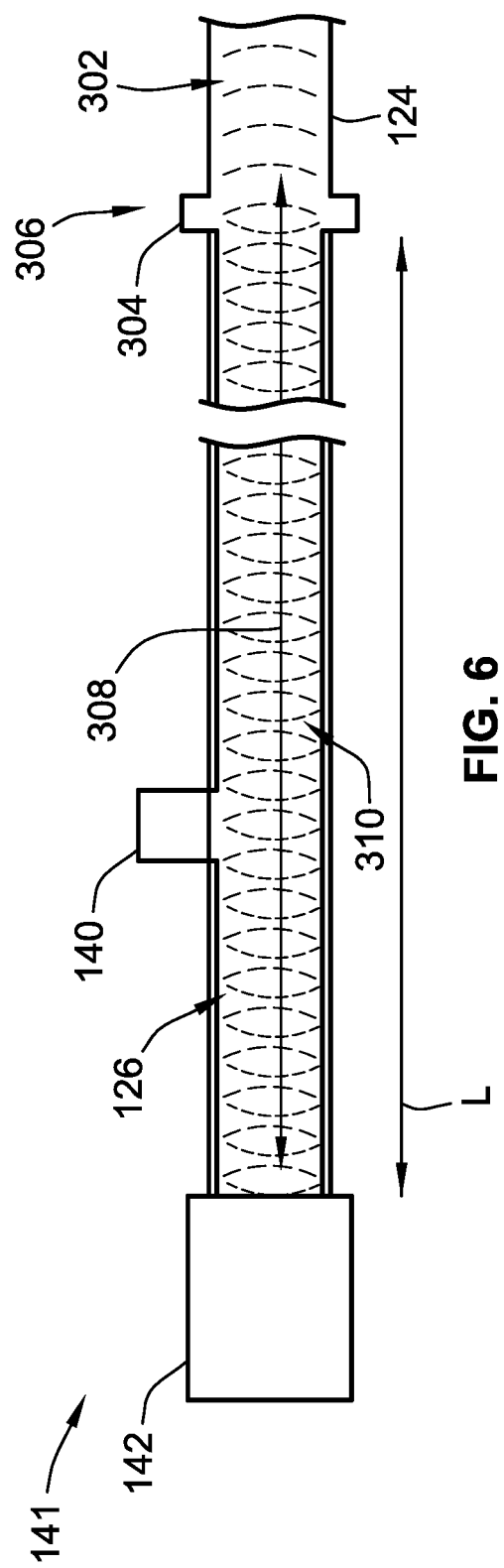
FIG. 6 illustrates the generation of acoustic data in response to an acoustic reflection indicative of one or more features of a user interface and/or a conduit, according to some implementations of the present disclosure.

In some implementations, the noise associated with operation of the respiratory therapy system is represented by on reflections of an acoustic signal propagating within the conduit, the user interface, and/or other component(s) of the respiratory therapy system. The acoustic data resulting from these reflections can be analyzed to generate a cepstrum, which represents various physical characteristics of the user interface, the conduit, or other components of the respiratory therapy system. These physical characteristics can aid in determining whether there is any liquid in the respiratory therapy system. FIG. 6 illustrates the generation of acoustic data in response to a reflection of an acoustic signal, according to aspects of the present disclosure. As shown in FIG. 6, the speaker 142 can be used to emit an acoustic signal 302 that propagates within the conduit 126. The microphone 140 can be used to detect the reflections 310 of the acoustic signal 302, and generate acoustic data representative of the reflections 310. In the illustrated implementations, the speaker 142 is used to generate and emit the acoustic signal 302. However, in other implementations, the speaker 142 can instead be replaced by another device that can generate an acoustic signal, such as the motor of the respiratory therapy device 122. The microphone 140 and speaker 142 are shown in specific locations relative to the conduit 126, which is connected to the respiratory therapy device 122 (not shown). However, the locations of the microphone 140 and the speaker 142 can vary from what is shown, as discussed above.

For example, FIG. 5 shows the microphone 140 in fluid communication with the interior of the conduit 126 but protruding from the periphery of the conduit 126. The housing of the microphone 140 could be coupled to the exterior of the conduit 126 over an aperture, such that the microphone 140 is in fluid communication with the interior of the conduit 126. The microphone 140 could also be placed within a duct that is coupled to the conduit 126 over an aperture. However, the microphone 140 can generally be disposed in any location where the microphone 140 is able to detect the required acoustic signals and/or reflections and generate the required acoustic data, as described herein. For example, the microphone 140 could be disposed entirely within the conduit 126. The microphone 140 can also be disposed generally anywhere within the air pathway that the conduit 126 is part of. As discussed herein, the respiratory therapy system 120 forms an air pathway that generally includes the motor of the respiratory therapy device 122, the user interface 124, the conduit 126, and any other elements or devices that may be used to deliver pressurized air to the user's airway. The microphone 140 can generally be placed anywhere within or adjacent to this air pathway, so long as the microphone 140 is in fluid communication (and/or acoustic communication) with the air pathway (e.g., is able to detect the acoustic reflections 310 (and/or any other desired acoustic signals and/or reflections) and generate acoustic data representative thereof).

The speaker 142 may emit the acoustic signal 302 within the conduit 126. The acoustic signal 302 is in the form of a sound. The sound can be one or more of a standard sound (e.g., an original, unmodified sound from an off-the-shelf sound application), a custom sound, an inaudible frequency, a white noise sound, a broad band impulse, a continuous sinusoidal waveform, a square waveform, a sawtooth waveform, and a frequency modulated sinusoid (e.g., chirp). Thus, as used herein, the "noise" associated with operation of the respiratory therapy system can include audible noise due to the presence of liquid, inaudible noise due to the presence of the liquid, an audible acoustic signal propagating in the conduit 126 or in other components of the respiratory therapy device, an inaudible acoustic signal propagating in the conduit 126 or in other components of the respiratory therapy device, or any combination thereof. According to some other implementations, the acoustic signal 302 can be in the form of one or more of an audible sound or an ultrasonic sound. According to some other implementations, the acoustic signal 302 is in the form of an inaudible sound, where the sound is inaudible based on one or both of the frequency of the sound (e.g., the frequency being outside of the frequency range for human hearing) or the amplitude of the sound (e.g., the amplitude being low enough that the sound is not loud enough for human perception).

In one or more implementations, the acoustic signal 302 is emitted at specific times, such as before the user first puts on the user interface, when the user first puts on the user interface, sometime after the user puts on the user interface, after the user takes off the user interface, after detecting that an apnea event or a hypopnea event is occurring (e.g., after detecting using a respiratory therapy device that an apnea event or a hypopnea event is occurring), and/or at predetermined time intervals. For example, the specific monitoring times are selected to be at intervals of 0.1 seconds for a duration of at least 4 seconds.

As the acoustic signal 302 travels down the length L of the conduit 126, the acoustic signal 302 can contact physical features of the conduit 126 and/or the user interface 124, such as feature 304. In FIG. 6, feature 304 is positioned at or near a connection of the user interface 124 with the conduit 126. In the illustrated implementation, the feature 304 includes a widening of a pathway 308 through which the acoustic signal 302 propagates, that is formed at the connection of the user interface 124 and the conduit 126. However, connection could also be a connection between the conduit 126 and the respiratory therapy device 122, the conduit 126 and another conduit, the conduit 126 and an elbow connector, an elbow connector and the user interface 124, or any other connection. In other implementations, the feature 304 could also be a narrowing of the pathway 308 due to the presence of liquid in the conduit 126. In either implementation, the change in the conduit 125 at the feature 304 causes a change in the acoustic impedance of the acoustic signal 302 and an acoustic reflection 310. In some implementations, the feature 304 is liquid in the conduit 126. The acoustic reflection 310 travels back down the length L of the conduit 126 until it reaches the microphone 140. The microphone 140 detects the acoustic reflection 310 and generates acoustic data in response to the acoustic reflection 310. The acoustic data is thus representative of the acoustic reflections 310 propagating within the conduit 126. The acoustic data may also be representative of the original acoustic signal 302, and any other acoustic signals (e.g., sound waves) that may be propagating within the conduit 126 and/or near the microphone 140. Liquid in a conduit 126 will cause a change in the cepstrum in a region corresponding to the conduit 126, and is typically characterized by a positive peak in the cepstrum plot corresponding to the point of occlusion (e.g. narrowing) caused by the liquid. One or more negative peaks in the cepstrum plot can correspond to the points of widening of the acoustic pathway in the vicinity of the point of occlusion of the conduit 126.

The microphone 140 can thus detect the reflections 310 due to the feature 304, as well as a variety of other reflections of the acoustic signal 302. In some implementations, the reflections 310 can be used to determine the length of the conduit. The acoustic data that is representative of the acoustic reflections 310 can be used to generate time-domain signals (such as time-domain intensity signals that represent the intensity and/or amplitude of the acoustic reflections 310 over a time period), frequency-domain signals (such as frequency-domain intensity signals that represent the intensity and/or amplitude of various different frequencies in the acoustic reflections 310), cepstrums, etc. In some implementations, the acoustic data represents a plurality of reflections from a plurality of acoustic signals, and thus the resulting intensity signals can represent the reflections of more than just the acoustic signal 302. For example, reflections from each of a plurality of acoustic signals can be averaged together, and the resulting signals can be generated from this average.

Liquid that has accumulated within the conduit 126 can alter the acoustic reflections 310 of the acoustic signal 302 that propagates within the conduit 126. Thus, by analyzing the acoustic data representing the acoustic reflections 310, it can be determined whether there is any liquid present in the conduit 126. In some implementations, the acoustic data representing the acoustic reflections can be analyzed to determine one or more physical characteristics of the conduit 126. The one or more physical characteristics of the conduit 126 can then be compared to baseline physical characteristics of the conduit 126, to aid in determining if any liquid is present in the conduit. For example, if liquid has accumulated within the conduit 126, the effective diameter of the conduit 126 through which the pressurized air flows may decrease, as discussed above (e.g., the narrowing of the pathway 308 due to the presence of liquid in the conduit 126). The acoustic data resulting from the acoustic reflections 310 can be analyzed to determine this effective diameter, which can then be compared to the actual diameter of the conduit 126. If the effective diameter of the conduit is less than the real diameter of the conduit 126, this indicates that there is liquid in the conduit 126. In another example, first and second cepstrums can be generated from the acoustic data at different times, and then compared to see if any liquid has accumulated in the conduit 126 during the time period separating the generation of the first cepstrum and the generation of the second cepstrum. For example, the first cepstrum could be generated before a sleep session, and a second cepstrum could be generated during or after the sleep session (during which session the user has used the respiratory therapy system).

While FIG. 6 illustrates the acoustic signal 302 be emitting into the conduit 126 by the speaker 142, any type of acoustic signal can be used to generate acoustic data in this manner. For example, the acoustic signal could be generated by the natural operation of the motor during operation of the respiratory therapy system; by an external device such as the user device 170, a white noise machine, etc.; or any other suitable mechanism. In some implementations, the acoustic signal can additionally or alternatively propagate within the user interface, the respiratory therapy device, or any other component of the respiratory therapy system. The acoustic data generated from the acoustic data can thus be used to analyze these other components of the respiratory therapy system, as well as the conduit 126.

Referring back to step 504 of method 500, in some implementations, the user can indicate to the system that there is liquid in the conduit or in another component of the respiratory therapy system. For example, if the user interface is wet or saturated when the user puts on the user interface or after the user has worn the user interface for a period of time, or if the user sees or hears liquid within the conduit, the user can use, for example, the user device 170 (which could be a smart phone, a tablet, a laptop, a smart speaker, etc.) to indicate to the system that there is liquid in the conduit or in another component of the respiratory therapy system. The system can use this user input in the detection of the presence of liquid in the respiratory therapy system, in addition to the acoustic data, as an alternative to the acoustic data, or as a confirmation of the detection based on the acoustic data.

In some implementations, other data such as temperature data and humidity data can be used in addition to (or in comes cases, as an alternative to) the acoustic data, to aid in detecting the presence of liquid in the conduit or elsewhere in the respiratory therapy system. For example, if it is determined that the temperature of the conduit or the ambient environment in which the conduit is located is colder than a predetermined threshold temperature at which condensation might be expected, this may indicate that there is a higher likelihood that some of the water vapor in the pressurized air has condensed into a liquid or will condense into a liquid. In another example, if the humidity within the conduit or the ambient environment in which the conduit is located is higher than a predetermined threshold humidity at which condensation might be expected, this may indicate that there is a higher likelihood that some of the water vapor in the pressurized air has condensed into a liquid or will condense into a liquid. Thus, the determination of whether there is any liquid within the conduit, the user interface, or any other component of the respiratory therapy system 120 can be based at least in part on temperature data, humidity data, or both.

In some implementations, the presence of the liquid is detected based at least in part by comparing a current measurement or signal with a previously-obtained baseline measurement or baseline signal. For example, the volume of noise occurring during the operation of the respiratory therapy system can be compared to a baseline volume known to occur when no liquid is present. In another example, time-domain or frequency-domain measurements can be compared to baseline time-domain or frequency-domain measurements obtained when it was known that no liquid was present in the respiratory therapy system. Any acoustic patterns or acoustic signatures analyzed using the acoustic data can be compared to baseline acoustic patterns or acoustic signatures obtained when it was known that no liquid was present in the respiratory therapy system.

At step 506 of the method 500, a variety of different actions can be taken, if the presence of liquid in the respiratory therapy system is detected. In some implementations, the action can include transmitting a notification to the user, and/or to a third party. The third party could be the user's spouse, roommate, family member, healthcare provider, or another person. The notification can include an indication to the user or to the third party that liquid has been detected in the respiratory therapy system. The notification can indicate to the user the specific location of the liquid within the respiratory therapy system (e.g., the housing of the respiratory therapy device, the user interface, the conduit, etc.), or can generally indicate that liquid has been detected.

In other implementations, a recommendation can additionally or alternatively be sent to the user and/or to the third party. The recommendation can include a recommendation on action to take in order to reduce or remove the liquid from the respiratory therapy system. In one example, the recommendation includes a recommendation to modify the temperature of the conduit. Rainout can occur when humidified air within the conduit cools down, and at least some of the water vapor condenses back into liquid. The temperature of the conduit can be increased in order to prevent water vapor from condensing back into a liquid and settling and/or pooling inside the conduit, such as on the internal surface of the conduit. In some implementations, the conduit includes a heating mechanism (such as thermally conductive wires within the walls of the conduit) that heats the conduit and the content of the conduit (air, liquid, etc.). In other implementations, the conduit can be heated by an external heating mechanism. In some implementations, the temperature of the conduit can be decreased, optionally after initially increasing the temperature to reduce or remove the liquid from the conduit.

In another example, the recommendation can include a recommendation to place a conduit jacket on the conduit. The conduit jacket can include an insulating material that at least partially covers the conduit. During operation of the respiratory therapy system, the humidified air cools down less as it passes through the conduit as a result of the conduit jacket insulating the conduit (and its contents) from the typically cooler ambient environment in which the conduit is located. The conduit jacket aids in preventing the water vapor from condensing back into liquid water, and accumulating in the conduit or in any other portion of the respiratory therapy system.

In a further example, the recommendation can include a recommendation to modify the temperature of a humidification tank of the respiratory therapy device (such as humidification tank 129). Generally, this modification will include decreasing the temperature of the humidification tank, which will reduce the amount of water vapor in the pressurized air traveling through the conduit. In turn, less water vapor will condense into liquid when in the conduit.

In an additional example, the recommendation can include a recommendation to adjust the temperature of the ambient environment surrounding the respiratory therapy system. For example, if the respiratory therapy system is located in the user's bedroom, the recommendation can include a recommendation to the user to adjust (e.g., increase) the temperature of the user's bedroom, in order to reduce the likelihood that liquid will accumulate in the respiratory therapy system.

In yet another example, the recommendation can include a recommendation to adjust the level of the liquid in the humidification tank. If the humidification tank is overfilled, liquid can spill out of the humidification tank into the housing of the respiratory therapy device. Operating the respiratory therapy system can carry this excess liquid to other components of the respiratory therapy system, including the user interface and the conduit. Reducing the amount of liquid within the humidification tank decreases the chances that any excess liquid will spill out of the humidification tank, and decreases the chance that any excess liquid will inadvertently flow to other components of the respiratory therapy system.

In an even further example, the recommendation can include a recommendation to dry the respiratory therapy device, the user interface, the conduit, or any other portion of the respiratory therapy system, and/or remove excessively humidified air from the conduit. For example, if the presence of liquid is detected in the conduit, the recommendation sent to the user can include a recommendation to detach the conduit from the respiratory therapy device and the user interface, and dry the conduit. Similarly, if the presence of liquid is detected in the user interface, the recommendation can include a recommendation to dry the user interface (and detach the user interface from the conduit if necessary). In some implementations, recommendation may include a recommendation for the user to forcefully exhale through the user interface and the conduit, in an effort to force any accumulated liquid out of the user interface and/or the conduit. The recommendation can also include a recommendation to detach the conduit from the respiratory therapy device, so that the pressurized air will not force the liquid back into the conduit once the respiratory therapy device begins operating. The recommendation could further include a recommendation to remove the user interface, so that the motor of the respiratory therapy device can be operated at a higher level to force liquid out of the conduit and out of the user interface, or operated in reverse to draw the liquid back into the respiratory therapy device. These actions would not typically be recommended during the sleep session (although they could be), as the user will likely already be wearing the user interface. However, this action could also be recommended to the user prior to the beginning of the sleep session, after the sleep session, or during the sleep session when the user is not using the respiratory therapy system.

In some implementations, the action can actions taken by the user and/or the respiratory therapy system, in order to reduce the amount of liquid in the respiratory therapy system, and/or prevent liquid from accumulating within the respiratory therapy system in the future. In one example, the action includes directly modifying the temperature of a variety of different components, instead of sending a recommendation to the user to modify the temperature of those components. For example, the respiratory therapy system could automatically adjust the temperature of the conduit when liquid is detected in the conduit or anywhere else. The respiratory therapy system could also adjust the temperature of the humidification tank or the ambient environment around the respiratory therapy system as needed. The user could also manually adjust the temperature of the conduit, the humidification tank, and/or the ambient environment; adjust the level of liquid in the humidification tank; place a conduit jacket on the conduit; dry the respiratory therapy device, the user interface, the conduit, and/or any other portion of the respiratory therapy system; remove excessively humidified air from the conduit; and other actions.

In another example, the operation of the respiratory therapy system can be modified in order to reduce the liquid within the respiratory therapy system. For example, if liquid is detected in the conduit and/or the user interface, the direction of operation of the motor of the respiratory therapy system can be reversed, to aid in drawing at least some of the liquid back into the respiratory therapy device, and out of the conduit. In another example, the operation of the motor can be adjusted to decrease the flow rate of the humidified air to aid in preventing any liquid within the respiratory therapy system from being carried by the pressurized air toward the user interface. In a further example, the motor can be operated at a higher level, to force liquid out of the conduit and out of the user interface. These actions could be manually performed by the user, and/or could automatically be performed by the respiratory therapy system.

In some implementations, the techniques of method 500 can implemented before the beginning of a sleep session. For example, when the user is getting ready for bed but before the sleep session has started (for example, before the user gets into bed or before the user begins to try to fall asleep), the acoustic data can be generated and analyzed to determine if there is any liquid in the user interface, the conduit, or another components of the respiratory therapy system. If liquid is detected, the user can be notified, so that the user can remove the liquid (for example by drying the user interface or emptying the conduit) before they begin their sleep session. Moreover, if the user detects that there is liquid in the user interface (for example if the user interface is wet or saturated when the user dons the user interface), in the conduit, or any other portion of the respiratory therapy system, the user can use the user device 170 to indicate to the system that there is liquid in the respiratory therapy system.

In other implementations, the techniques of method 500 can be implemented during a sleep session. For example, the acoustic data can be generated during the sleep session, and if the analysis of the acoustic data indicates that there is liquid within the user interface, the conduit, or any other portion of the respiratory therapy system, actions can be taken to reduce or remove this liquid. Because the user is likely to be asleep during the sleep session, the action will generally be of the type that does not require any user involvement (such as modifying the temperature of the conduit, temporarily reversing the direction of the motor, etc.). However, the action can also include generating a notification and a recommendation to prevent the occurrence of rainout in future sleep sessions, that the user can view once the sleep session ends. Thus, the user can wake up to a notification that liquid was detected somewhere in the respiratory therapy system, and to a recommendation to prevent the formation of this liquid during subsequent sleep sessions. In some of these implementations, the system can detect whether the user is awake, and the action can be adjusted accordingly. For example, if the presence of liquid in the respiratory therapy system is detected when the user is awake during the sleep session, the system can send the user a recommendation for immediate action to remove or reduce the liquid in the respiratory therapy system.

Many of the actions performed by the user could also be automated actions. For example, if the action includes adjusting the temperature and/or humidity of the respiratory therapy system, this action could be manually performed by the user, or could automatically be performed by the respiratory therapy system itself.

In a further implementation, the techniques of method 500 can be implemented after the sleep session ends. The respiratory therapy system can be operated normally during the sleep session, and once the sleep session ends (e.g., once the user wakes up and gets out of bed), the acoustic data can be generated and analyzed to determine if any liquid accumulated within the respiratory therapy system during the sleep session.

Figure 7:
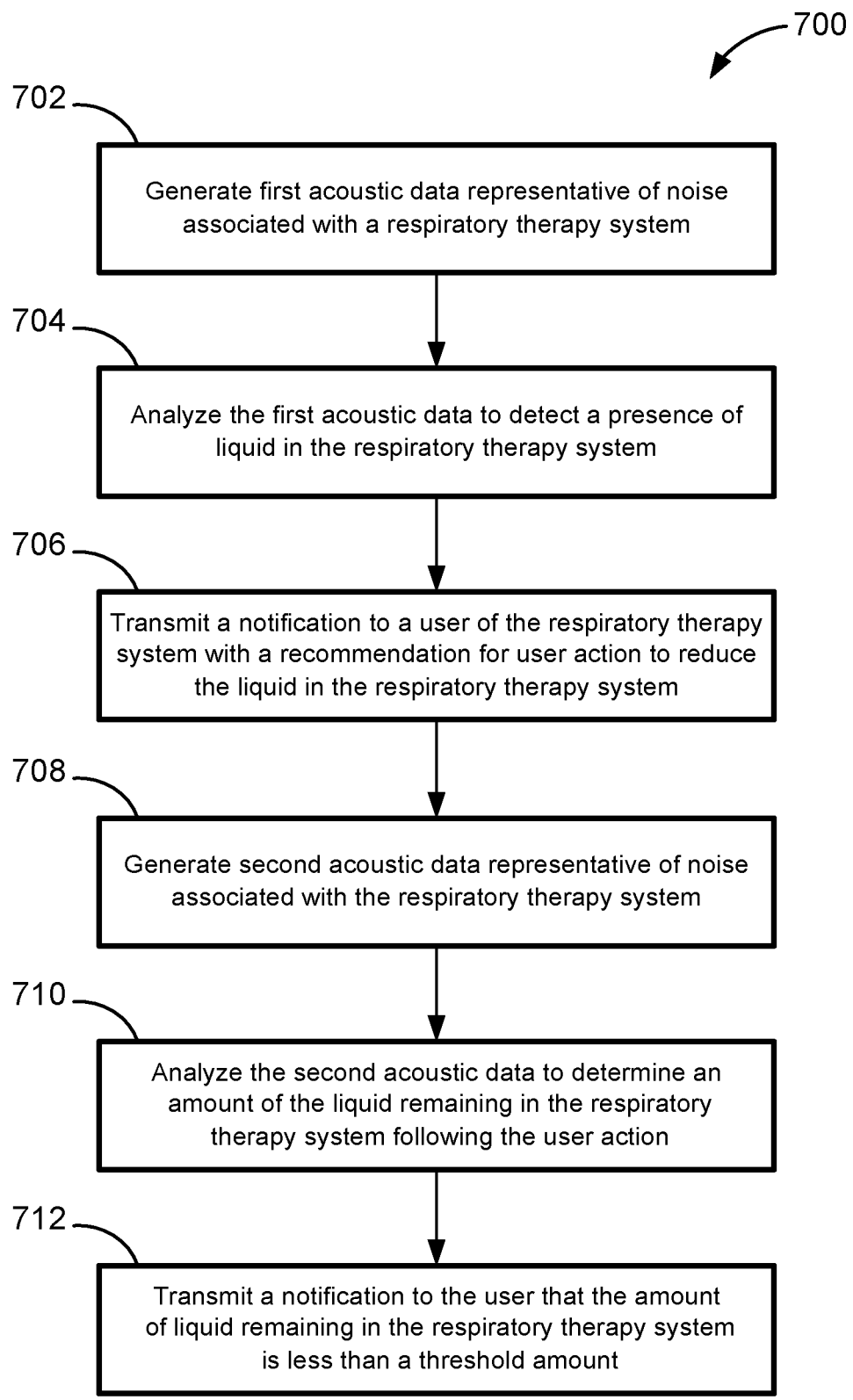
FIG. 7 is a flow diagram of a process for detecting rainout in a respiratory therapy system, according to some implementations of the present disclosure.

FIG. 7 illustrates a method 700 for detecting rainout in a respiratory therapy system (such as respiratory therapy system 120) that includes a respiratory therapy device configured to supply pressurized air (such as respiratory therapy device 122), and a user interface (such as user interface 124) coupled to the respiratory therapy device via a conduit (such as conduit 126). The user interface is configured to engage with the user, and aids in directing the pressurized air to the user's airway. Generally, a control system having one or more processors (such as control system 110 of system 100) is configured to carry out the steps of method 700. A memory device (such as memory device 114 of system 100) can be used to store machine-readable instructions that are executed by the control system to carry out the steps of method 700. The memory device can also store any type of data utilized in the steps of method 700. Generally, method 700 can be implemented using a system (such as system 100) that includes the respiratory therapy system, the control system, and the memory device.

Step 702 of method 700 is similar to step 502 of method 500, and includes generating first acoustic data using one or more microphones. The first acoustic data is representative of noise occurring in the location of the respiratory therapy system, including noise that is representative of or characteristic of liquid (if present) in the respiratory therapy system. Step 704 of method 700 is similar to step 504 of method 500, and includes analyzing the first acoustic data to detect the presence of liquid in the respiratory therapy system. The analysis of the first acoustic data can utilize the same techniques discussed herein with respect to step 504 of method 500. Further, other types of data can also be analyzed to aid in determining whether there is any liquid in the respiratory therapy system, including temperature data, humidity data, input received from the user, and other data.

Step 706 of method 700 includes transmitting a notification to the user (or a third party such as a spouse, roommate, family member, healthcare provider, etc.) with a recommendation for removing or reducing the amount of liquid in the respiratory therapy system, and/or for preventing the future accumulation of liquid in the respiratory therapy system. Generally, the recommendation will include a recommendation for the user to take some sort of action to prevent the liquid from accumulating within the respiratory therapy system in the future. Thus, the recommendation can include a recommendation to increase the temperature of the conduit, a recommendation to reduce the level of liquid within the humidification tank, a recommendation to dry out the user interface and/or the conduit via any suitable technique discussed herein, or any other suitable recommendation. The recommendation can additionally or alternatively include a recommendation for the user to cause and/or allow the respiratory therapy system to automatically make a variety of different adjustments to remove or reduce the amount if liquid in the respiratory therapy system, and/or to prevent the future accumulation of liquid in the respiratory therapy system.

Step 708 of method 700 includes generating second acoustic data that is representative of noise occurring in the area around the respiratory therapy system, including noise that is representative of or characteristic of liquid (if present) in the respiratory therapy system. The second acoustic data can be generated using one or more microphones. Generally, the second acoustic data is generated after the recommended action has been taken. Step 710 includes analyzing the second acoustic data to determine the amount (if any) of liquid remaining in the respiratory therapy system following the action. The analysis of the second acoustic data can utilize the same techniques discussed herein with respect to step 704 of method 700, or step 504 of method 500. Further, other types of data can also be analyzed to aid in determining whether there is any liquid in the respiratory therapy system, including temperature data, humidity data, input received from the user, and other data.

Finally, at step 712, a notification can be transmitted to the user if the amount of liquid remaining in the respiratory therapy system satisfied a predetermined threshold amount. In some implementations, the notification is transmitted to the user if the amount of liquid remaining is above the predetermined threshold amount. In these implementations, the user is thus notified if the action was not successful. The notification in these implementations may thus also include a new recommendation for action to remove the liquid or prevent the future accumulation of the liquid. In other implementations, the notification is transmitted if the amount of liquid remaining is below the predetermined threshold amount. In these implementations, the user is thus notified if the action was successful in removing the liquid or prevent the future accumulation of the liquid. In still other implementations, the user is notified both if the amount of liquid remaining is above the predetermined threshold amount, and if the amount of liquid remaining is below the predetermined threshold amount.

In some implementations, the first acoustic data is generated and analyzed prior to the beginning of the sleep session, for example prior to the user getting into bed, or prior to the user donning the user interface and beginning the operation of the respiratory therapy system. In some of these implementations, the second acoustic data is also generated and analyzed prior to the beginning of the sleep session. In others of these implementations, the second acoustic data can be generated and analyzed at some point or points during the sleep session (for example if the user wakes up during the sleep session). These implementations could include a one-time monitoring and/or detection of liquid in the conduit (or other component of the respiratory therapy system), multiple-time monitoring and/or detection of liquid in the conduit (or other component of the respiratory therapy system), or continuous monitoring and/or detection of liquid in the conduit (or other component of the respiratory therapy system). The second acoustic data can also be generated and analyzed after the sleep session has ended (for example after the user takes off the user interface and/or gets out of bed).

In some implementations, the first acoustic data is generated and analyzed during the sleep session. For example, if the user wakes up at any point during the night, the system can take the opportunity to generate and analyze the first acoustic data to see if any liquid has accumulated within the respiratory therapy system. If so, the user can act to remove the liquid from the respiratory therapy system and/or to prevent additional liquid from accumulating within the respiratory therapy system during the remainder of the sleep session (either by direct action or by causing or allowing the respiratory therapy system to take action). Thus, the user may be asleep prior to the first acoustic data being generated and analyzed, but may be awake when the first acoustic data is generated and analyzed. The second acoustic data could be generated and analyzed before the user falls back asleep, or could be generated and analyzed after the sleep session ends.

In still other implementations, the first acoustic data can be generated and analyzed after the end of a sleep session, and the user can take action to remove any accumulated liquid in the respiratory therapy system and/or prevent the future accumulation of liquid in the respiratory therapy system after the sleep session (either by direct action or by causing or allowing the respiratory therapy system to take action). The second acoustic data can then be generated and analyzed at any point prior to a subsequent sleep session, or at any point after a subsequent sleep session.

Thus, method 700 can be used to determine the efficacy of a variety of different techniques for removing liquid from the respiratory therapy system, and/or for preventing liquid from accumulating within the respiratory therapy system during future sleep session.

Generally, methods 500 and 700 can be implemented using a system having a control system with one or more processors, and a memory device storing machine readable instructions. The control system can be coupled to the memory device, and methods 500 and 700 can be implemented when the machine readable instructions are executed by at least one of the processors of the control system. Methods 500 and 700 can also be implemented using a computer program product (such as a non-transitory computer readable medium) comprising instructions that when executed by a computer, cause the computer to carry out the steps of methods 500 and 700.

One or more elements or aspects or steps, or any portion(s) thereof, from one or more of any of the claims can be combined with one or more elements or aspects or steps, or any portion(s) thereof, from one or more of any of the other claims or combinations thereof, to form one or more additional implementations and/or claims of the present disclosure.

While the present disclosure has been described with reference to one or more particular embodiments or implementations, those skilled in the art will recognize that many changes may be made thereto without departing from the spirit and scope of the present disclosure. Each of these implementations and obvious variations thereof is contemplated as falling within the spirit and scope of the present disclosure. It is also contemplated that additional implementations or alternative implementations according to aspects of the present disclosure may combine any number of features from any of the implementations described herein, such as, for example, in the alternative implementations described below.

What is claimed is:

1. A method of detecting rainout in a respiratory therapy system, the respiratory therapy system including a respiratory therapy device, a user interface coupled to the respiratory therapy device via a conduit, at least one microphone, and a control system, the method comprising:
   generating, via the at least one microphone, first acoustic data representative of noise associated with the respiratory therapy system;
   analyzing, via the control system, the first acoustic data to detect a presence of liquid in the respiratory therapy system;
   transmitting, to the user of the respiratory therapy system, (i) a notification of the presence of the liquid in the respiratory therapy system and (ii) a recommendation for action to reduce or remove the liquid in the respiratory therapy system;
   generating, via the at least one microphone, second acoustic data representative of noise associated with the respiratory therapy system;
   analyzing, via the control system, the second acoustic data to determine an amount of the liquid remaining in the respiratory therapy system following the action; and
   in response to determining that the amount of the liquid remaining in the respiratory therapy system is less than a threshold amount, transmitting to the user, a notification that the amount of liquid remaining in the respiratory therapy system is less than the threshold amount.

2. The method of claim 1, wherein the first acoustic data is generated prior to a beginning of a sleep session, during the sleep session, or prior to the user donning the user interface of the respiratory therapy system, or wherein the user is asleep prior to the generation of the first acoustic data and awake during the generation of the first acoustic data.

3. The method of claim 1, wherein the noise associated with the respiratory therapy system is caused by the presence of the liquid in the conduit, in the user interface, or both.

4. The method of claim 3, wherein the noise caused by the presence of the liquid in the respiratory therapy system results in a corresponding acoustic signature in the first acoustic data, the second acoustic data, or both the first acoustic data and the second acoustic data, and wherein analyzing the first acoustic data, the second acoustic data, or both the first acoustic data and the second acoustic data includes identifying the acoustic signature of the noise caused by the presence of the liquid in the respiratory therapy system.

5. The method of claim 3, wherein analyzing the first acoustic data, the second acoustic data, or both the first acoustic data and the second acoustic data includes:
generating a frequency spectrum from the first acoustic data, the second acoustic data, or both the first acoustic data and the second acoustic data; and
identifying one or more features of the frequency spectrum that are indicative of the presence of the liquid.

6. The method of claim 3, wherein analyzing the first acoustic data, the second acoustic data, or both the first acoustic data and the second acoustic data includes:
generating a mel-frequency cepstrum from the first acoustic data, the second acoustic data, or both the first acoustic data and the second acoustic data; and
determining one or more mel-frequency cepstral coefficients from the mel-frequency cep strum,
wherein the detection of the presence of the liquid is based at least in part on the one or more mel-frequency cepstral coefficients.

7. The method of claim 6, wherein analyzing the first acoustic data, the second acoustic data, or both the first acoustic data and the second acoustic data further includes inputting the one or more mel-frequency cepstral coefficients into a machine learning model configured to detect the presence of the liquid based at least in values of the one or more mel-frequency cepstral coefficients.

8. The method of claim 3, wherein the noise is represented by one or more reflections of an acoustic signal propagating in the conduit, and wherein analyzing the first acoustic data, the second acoustic data, or both the first acoustic data and the second acoustic data includes generating a cepstrum from the first acoustic data, the second acoustic data, or both the first acoustic data and the second acoustic data and analyzing the cepstrum to identify the presence of the liquid in the conduit, the cep strum being indicative of one or more physical features in the conduit, the one or more physical features in the conduit including the liquid in the conduit.

9. The method of claim 8, wherein analyzing the cep strum includes identifying one or more features of the cepstrum that are indicative of a reflection of the acoustic signal due to the presence of the liquid in the conduit, the one or more features of the cepstrum including an acoustic signature of the noise.

10. The method of claim 8, wherein analyzing the cep strum includes:
determining an effective diameter of the conduit; and
comparing the effective diameter of the conduit to a real diameter the conduit,
wherein the effective diameter of the conduit is less than the real diameter of the conduit indicates the presence of the liquid in the conduit.

11. The method of claim 8, wherein analyzing the first acoustic data, the second acoustic data, or both the first acoustic data and the second acoustic data includes:
generating a first cepstrum from the first acoustic data, the second acoustic data, or both the first acoustic data and the second acoustic data at a first time;
generating a second cepstrum from the first acoustic data, the second acoustic data, or both the first acoustic data and the second acoustic data at a second time after the first time; and
comparing the first cep strum and the second cepstrum, one or more differences between the first cep strum and the second cep strum being indicative of the presence of the liquid.

12. The method of claim 8, wherein the acoustic signal is emitted by a speaker and directed through the conduit of the respiratory therapy system, wherein the acoustic signal is emitted by a motor of the respiratory therapy system, or both.

13. The method of claim 1, wherein analyzing the first acoustic data, the second acoustic data, or both the first acoustic data and the second acoustic data includes determining a volume level of the noise associated with the respiratory therapy system, and wherein the detection of the presence of the liquid in the conduit is based at least in part on the volume level of the noise, and wherein the method further comprises determining an amount of the liquid in the respiratory therapy system based at least in part on the volume level of the noise.

14. The method of claim 1, wherein the action includes modifying a temperature of the conduit, modifying a temperature of a humidification tank of the respiratory therapy system, modifying a temperature of an ambient environment around the conduit, reversing a direction of a motor of the respiratory therapy system, increasing a rate of flow of pressurized air through the conduit, adjusting a level of liquid in the humidification tank, placing a conduit jacket on the conduit, replacing the conduit, drying the conduit, or any combination thereof.

15. The method of claim 1, wherein:
the first acoustic data, the second acoustic data, or both the first acoustic data and the second acoustic data is generated prior to a beginning of a sleep session, and the action includes reducing or removing the liquid in the respiratory therapy system prior to the beginning of the sleep session; or
the first acoustic data, the second acoustic data, or both the first acoustic data and the second acoustic data is generated during or after a completion of a first sleep session and the action includes reducing or removing the liquid in the respiratory therapy system prior to a beginning of a second sleep session after the first sleep session.

16. The method of claim 1, wherein the first acoustic data, the second acoustic data, or both the first acoustic data and the second acoustic data is generated during a sleep session, and wherein the action includes increasing a temperature of the conduit, decreasing a temperature of a humidification tank of the respiratory therapy sy stem, increasing a temperature of an ambient environment around the conduit, reversing a direction of a motor of the respiratory therapy system, increasing a rate of flow of pressurized air through the conduit, or any combination thereof.

17. The method of claim 1, further comprising receiving input from the user indicative of the presence of the liquid in the respiratory therapy system, wherein the action is based at least in part on the input from the user.

18. The method of claim 1, further comprising determining a temperature outside the conduit, a humidity outside the conduit, or both, wherein the detection of the presence of the liquid in the respiratory therapy system is based at least partially on the temperature outside the conduit, the humidity outside the conduit, or both.

19. A system comprising:
a respiratory therapy system including:
a respiratory therapy device configured to supply pressurized air; and a user interface coupled to the respiratory therapy device via a conduit, the user interface being configured to engage a user and aid in directing the supplied pressurized air to an airway of the user;

at least one microphone;

a memory device storing machine-readable instructions; and a control system coupled to the memory device, the control system including one or more processors configured to execute the machine-readable instructions to:

generate, via the least one microphone, first acoustic data representative of noise associated with the respiratory therapy system;

analyze the first acoustic data to detect a presence of liquid in the respiratory therapy system;

transmit, to the user of the respiratory therapy system, (i) a notification of the presence of the liquid in the respiratory therapy system and (ii) a recommendation for action to reduce or remove the liquid in the respiratory therapy system;

generate, via the at least one microphone, second acoustic data representative of noise associated with the respiratory therapy system;

analyze the second acoustic data to determine an amount of the liquid remaining in the respiratory therapy system following the action; and in response to determining that the amount of the liquid remaining in the respiratory therapy system is less than a threshold amount, transmit to the user a notification that the amount of liquid remaining in the respiratory therapy system is less than the threshold amount.

20. The system of claim 19, wherein the first acoustic data is generated prior to a beginning of a sleep session, during the sleep session, or prior to the user donning the user interface, or wherein the user is asleep prior to the generation of the first acoustic data and awake during the generation of the first acoustic data.

21. The system of claim 19, wherein the noise associated with the respiratory therapy system is caused by the presence of the liquid in the conduit, in the user interface, or both.

22. The system of claim 21, wherein the noise caused by the presence of the liquid in the respiratory therapy system results in a corresponding acoustic signature in the first acoustic data, the second acoustic data, or both the first acoustic data and the second acoustic data, and wherein analyzing the first acoustic data, the second acoustic data, or both the first acoustic data and the second acoustic data includes identifying the acoustic signature of the noise caused by the presence of the liquid in the respiratory therapy system.

23. The system of claim 21, wherein analyzing the first acoustic data, the second acoustic data, or both the first acoustic data and the second acoustic data includes:

generating a frequency spectrum from the first acoustic data, the second acoustic data, or both the first acoustic data and the second acoustic data; and identifying one or more features of the frequency spectrum that are indicative of the presence of the liquid.

24. The system of claim 21, wherein analyzing the first acoustic data, the second acoustic data, or both the first acoustic data and the second acoustic data includes:

generating a mel-frequency cepstrum from the first acoustic data, the second acoustic data, or both the first acoustic data and the second acoustic data; and determining one or more mel-frequency cepstral coefficients from the mel-frequency cep strum, wherein the detection of the presence of the liquid is based at least in part on the one or more mel-frequency cepstral coefficients.

25. The system of claim 24, wherein analyzing the first acoustic data, the second acoustic data, or both the first acoustic data and the second acoustic data further includes inputting the one or more mel-frequency cepstral coefficients into a machine learning model configured to detect the presence of the liquid based at least in values of the one or more mel-frequency cepstral coefficients.

26. The system of claim 21, wherein the noise is represented by one or more reflections of an acoustic signal propagating in the conduit, and wherein analyzing the first acoustic data, the second acoustic data, or both the first acoustic data and the second acoustic data includes generating a cepstrum from the first acoustic data, the second acoustic data, or both the first acoustic data and the second acoustic data and analyzing the cep strum to identify the presence of the liquid in the conduit, the cep strum being indicative of one or more physical features in the conduit, the one or more physical features in the conduit including the liquid in the conduit.

27. The system of claim 26, wherein analyzing the cep strum includes identifying one or more features of the cepstrum that are indicative of a reflection of the acoustic signal due to the presence of the liquid in the conduit, the one or more features of the cep strum including an acoustic signature of the noise.

28. The system of claim 26, wherein analyzing the cepstrum includes:

determining an effective diameter of the conduit; and comparing the effective diameter of the conduit to a real diameter the conduit, wherein the effective diameter of the conduit is less than the real diameter of the conduit indicates the presence of the liquid in the conduit.

29. The system of claim 26, wherein analyzing the first acoustic data, the second acoustic data, or both the first acoustic data and the second acoustic data includes:

generating a first cep strum from the first acoustic data, the second acoustic data, or both the first acoustic data and the second acoustic data at a first time;

generating a second cepstrum from the first acoustic data, the second acoustic data, or both the first acoustic data and the second acoustic data at a second time after the first time; and comparing the first cep strum and the second cepstrum, one or more differences between the first cep strum and the second cep strum being indicative of the presence of the liquid.

30. The system of claim 26, wherein the acoustic signal is emitted by a speaker and directed through the conduit, wherein the acoustic signal is emitted by a motor of the respiratory therapy system, or both.

31. The system of claim 19, wherein analyzing the first acoustic data, the second acoustic data, or both the first acoustic data and the second acoustic data includes determining a volume level of the noise associated with the respiratory therapy system, and wherein the detection of the presence of the liquid in the conduit is based at least in part on the volume level of the noise, and wherein the one or more processors of the control system are further configured to determine an amount of the liquid in the respiratory therapy system based at least in part on the volume level of the noise.

32. The system of claim 19, wherein the action includes modifying a temperature of the conduit, modifying a temperature of a humidification tank of the respiratory therapy system, modifying a temperature of an ambient environment around the conduit, reversing a direction of a motor of the respiratory therapy system, increasing a rate of flow of pressurized air through the conduit, adjusting a level of liquid in the humidification tank, placing a conduit jacket on the conduit, replacing the conduit, drying the conduit, or any combination thereof.

33. The system of claim 19, wherein:
- the first acoustic data, the second acoustic data, or both the first acoustic data and the second acoustic data is generated prior to a beginning of a sleep session, and the action includes reducing or removing the liquid in the respiratory therapy system prior to the beginning of the sleep session; or
- the first acoustic data, the second acoustic data, or both the first acoustic data and the second acoustic data is generated during or after a completion of a first sleep session and the action includes reducing or removing the liquid in the respiratory therapy system prior to a beginning of a second sleep session after the first sleep session.

34. The system of claim 19, wherein the first acoustic data, the second acoustic data, or both the first acoustic data and the second acoustic data is generated during a sleep session, and wherein the action includes increasing a temperature of the conduit, decreasing a temperature of a humidification tank of the respiratory therapy system, increasing a temperature of an ambient environment around the conduit, reversing a direction of a motor of the respiratory therapy system, increasing a rate of flow of pressurized air through the conduit, or any combination thereof.

35. The system of claim 19, wherein the one or more processors of the control system are further configured to execute the machine-readable instructions to receive system input from the user indicative of the presence of the liquid in the respiratory therapy system, a presence of the liquid in the user interface, or both, wherein the action is based at least in part on the input from the user.

36. The system of claim 19, wherein the one or more processors of the control system are further configured to execute the machine-readable instructions to determines a temperature outside the conduit, a humidity outside the conduit, or both, wherein the detection of the presence of the liquid in the respiratory therapy system is based at least partially on the temperature outside the conduit, the humidity outside the conduit, or both.

* * * * *